United States Patent [19]

Lednicer

[11] 4,200,588
[45] Apr. 29, 1980

[54] POLYCYCLOANILINES

[75] Inventor: Daniel Lednicer, Portage, Mich.

[73] Assignee: The Upjohn Company, Kalamazoo, Mich.

[21] Appl. No.: 800,799

[22] Filed: May 26, 1977

Related U.S. Application Data

[60] Division of Ser. No. 576,342, May 12, 1975, Pat. No. 4,036,977, which is a continuation-in-part of Ser. No. 507,462, Sep. 19, 1974, abandoned, which is a continuation-in-part of Ser. No. 416,402, Nov. 16, 1973, abandoned.

[51] Int. Cl.² ............................................. C07C 93/14
[52] U.S. Cl. .................................................. 260/571
[58] Field of Search .................. 260/570.5 P, 570.8 R, 260/571, 578

[56] References Cited

U.S. PATENT DOCUMENTS 3,169,941  2/1965  Alt et al. ........................ 260/571 X

Primary Examiner—Robert V. Hines
Attorney, Agent, or Firm—Martin B. Barancik

[57] ABSTRACT

Compounds of the formula

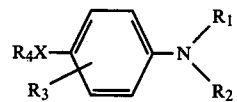

where $R_4X$ is a polycyclocoupled group and $R_1$ and $R_2$ are H or simple hydrocarbon and $R_3$ has the same value and additionally simple acyl, can be made by a variety of syntheses. They have hypolipedemic and antiatherosclerotic properties, and are useful in that field.

13 Claims, No Drawings

POLYCYCLOANILINES

CROSS REFERENCE TO RELATED APPLICATIONS

This application is a division of co-pending Ser. No. 576,342, and now U.S. Pat. No. 4,036,977, filed May 12, 1975, which is a continuation-in-part of application Ser. No. 507,462, filed Sept. 19, 1974, which is a continuation-in-part of application Ser. No. 416,402, filed Nov. 16, 1973 both now abandoned.

BRIEF SUMMARY OF THE INVENTION

The compounds of this invention are useful as hypolipidemic agents, particularly hypocholesteremic and are useful in the treatment of serum lipid disorders and other disorders of lipid metabolism including the various types of hyperlipoproteinemia and other hyperlipidemias. The route of administration is preferably oral, and the usual oral modes of administration and dosage forms are used. Parenteral and rectal routes of administration are also possible.

In standard cholesterol fed laboratory test animals (e.g. the rat, the gerbil and the quail) the compounds of the invention (A) are effective in controlling both low density lipoproteins (LDL) and very low density lipoproteins (VLDL). In the tabulated data which is presented subsequently the activity is evinced by either the heparin precipitate $A_{680}$ and/or the cholesterol content. The critical effect is a lowering of either value (heparin precipitate or cholesterol) compared with the control data. Dosages (daily) in rats in the range of 25 and over miligrams per kilogram were found to be significantly active. The effects found in the experimental animals is expected to be translatable to humans and the compounds of (A) are conceived to provide prophylaxis against such diseases as atherosclerosis and arteriosclerosis is humans.

The compounds (A) of this invention can be prepared for administration to patients in unit dosage form such as tablets, capsules, pills, powders, granules, oral solutions or suspensions, oil-in-water and water-in-oil emulsions, suppositories and sterile solutions or suspensions for injections containing suitable quantities of (A).

For oral administration either solid or fluid unit dosage forms can be prepared. For preparing solid compositions such as tablets, (A) is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in water together with sweetening agents, flavoring agents, and a sugar, with preservatives, to form a syrup. The elixirs can be prepared using an aqueous alcoholic vehicle such as aqueous ethanol with suitable sweeteners such as sugar and saccharin, together with an aromatic flavoring agent. Suspensions can be prepared with a syrup vehicle with the aid of a suspending agent such as acacia, tragacanth, methylcellulose and the like. Adult human daily dosage is in the range of 0.1 g. to 10 g., preferably 0.5 g. to 3 g.

The compounds of this invention have the formula:

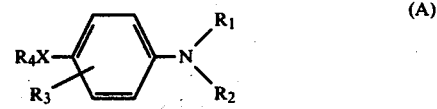
(A)

in which

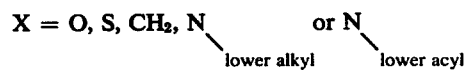

$R_1$ = hydrogen,
lower alkyl amino in which the alkyl group is from 1 to 6 carbon atoms,
alkyl of 1 to 8 carbon atoms,
$(CH_2)_n$-Phenyl,
lower alkynyl of 1 to 6 carbon atoms,
$(CH_2)_n$-O-Phenyl,

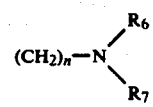

in which $R_6$ and $R_7$ = lower alkyl groups of 1 to 6 carbon atoms, or
$(CH_2)_n$—OH,
n = 1, 2, or 3.
$R_2$ = hydrogen,
lower alkyl of from 1 to 6 carbon atoms,
lower aliphatic acyl of from 1 to 6 carbon atoms, $$\overset{O}{\underset{}{\overset{\|}{C}}}-O-\text{alkyl}$$

in which alkyl is 1 to 6 carbon atoms.
$R_1, R_2$ = together $(CH_2)_m$ where m is 4 to 12,

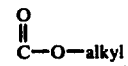

where $R_5$ is lower alkyl of from 1 to 6 carbon atoms,

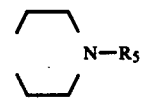

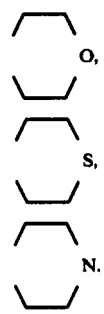

$R_3$ = hydrogen,
halogen,
3-methyl,

-continued 5-methyl,
2,6-dimethyl,
3,5-dimethyl,
—CHO,
—CH$_2$OH,
—CH(CH$_3$)OH, 3-N$\begin{smallmatrix}R_1\\R_2\end{smallmatrix}$ , 1-N$\begin{smallmatrix}R_1\\R_2\end{smallmatrix}$ ,

—CH$_2$—S—CH$_3$.

R$_4$=a bridged polycyclic hydrocarbon attached through a tertiary carbon atom.

Lower alkyl in the above means alkyl of from 1 to 5 carbon atoms, and lower acyl means acyl of from 1 to 5 carbon atoms.

Examples of R$_4$ are:

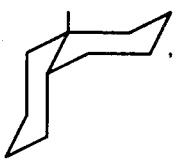

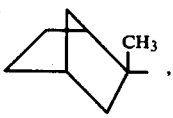

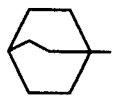

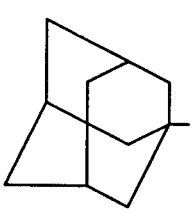

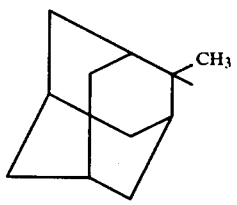

-continued

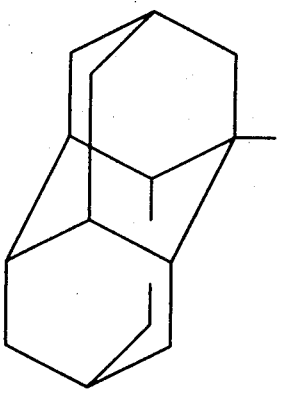

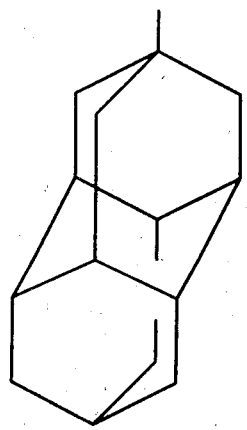, and

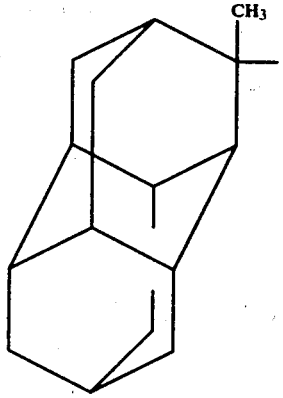

Preferred compounds of this invention have the formula:

in which R$_1$, R$_2$, R$_3$ and R$_4$ have the same meanings as R$_1$, R$_2$, R$_3$ and R$_4$ defined above.

The general methods for synthesising the compounds of this invention are represented by the following syntheses steps. In the steps R$_4$ can be

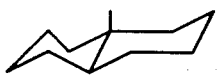

-continued
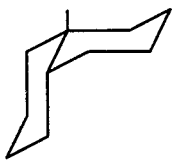,
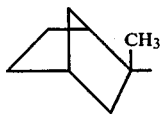,
,
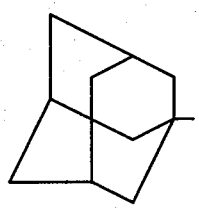
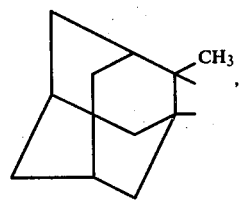,
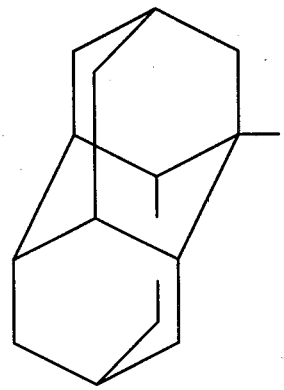,
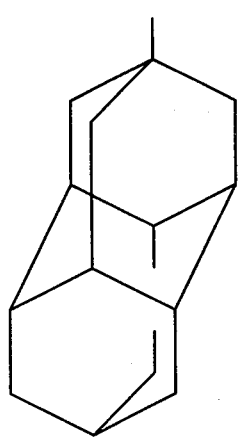, or
-continued
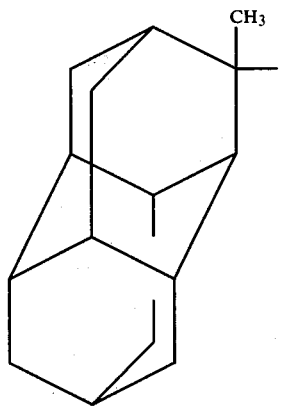
The reaction conditions that are significant are indicated. It is to be understood that equivalent conditions and reactants can be substituted without departing from the invention.
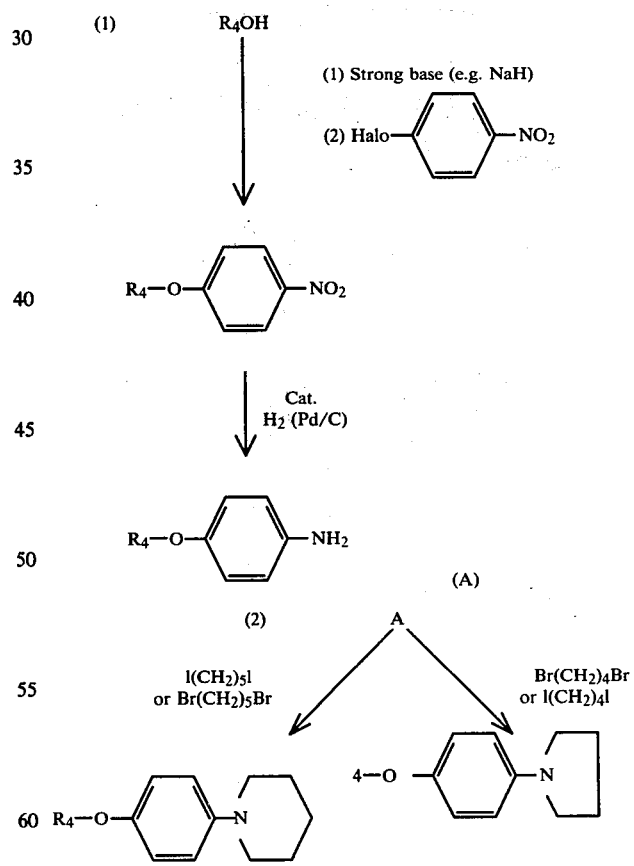
In the above and following reactions "Halo" means halogen, "Cat." means catalyzed, "Pd/C" means palladium on charcoal and "BuLi" means butyl lithium.

(3)
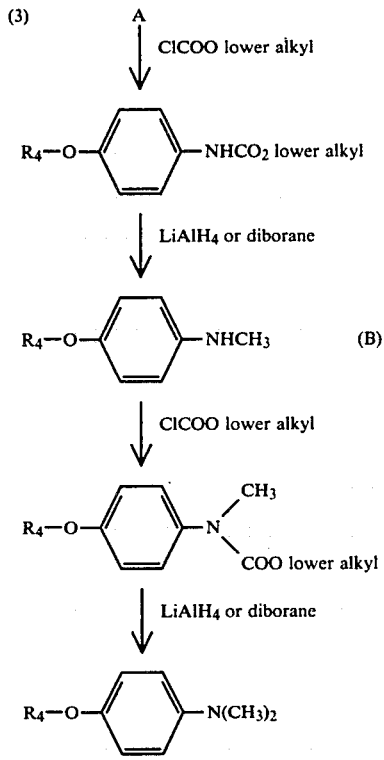
(4)
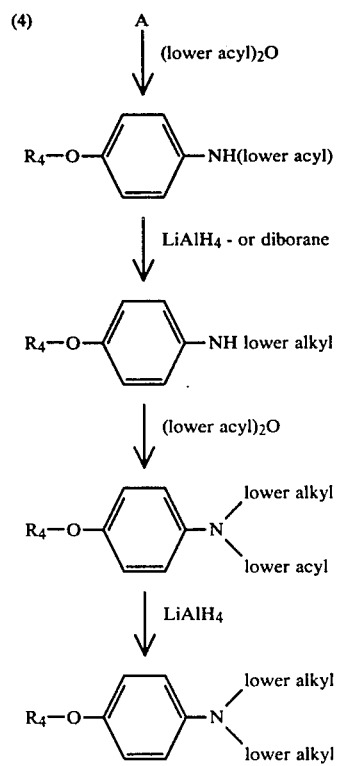
(5)
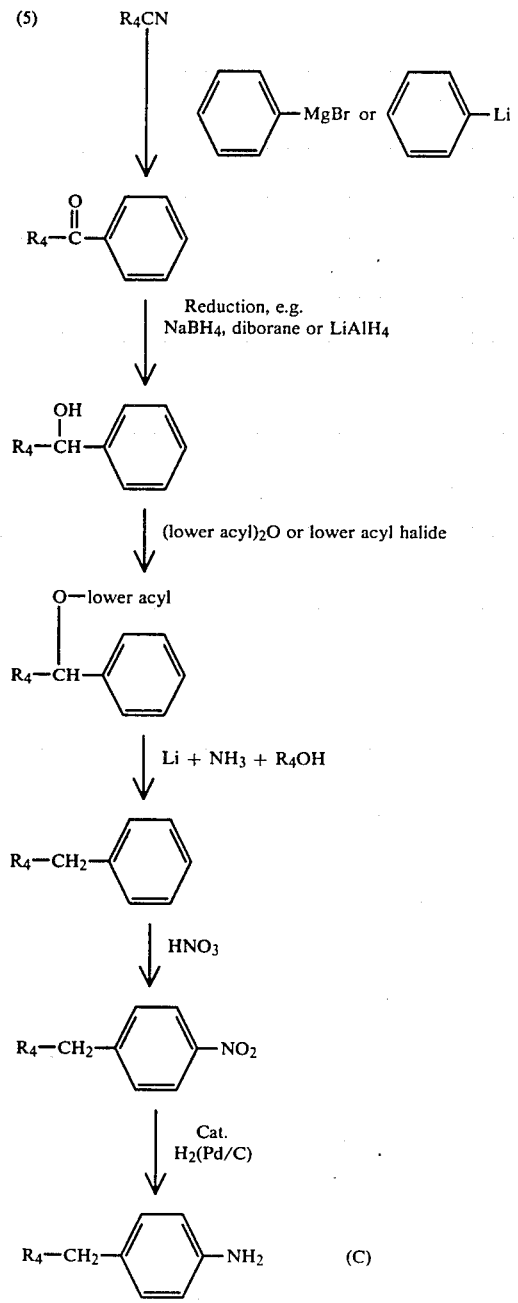

-continued
(6)
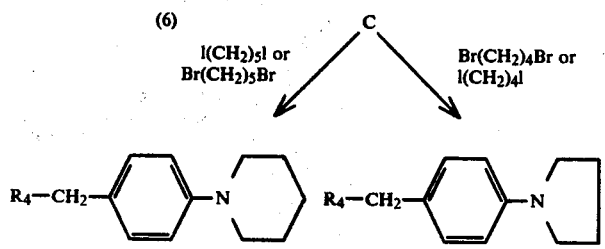
(7)
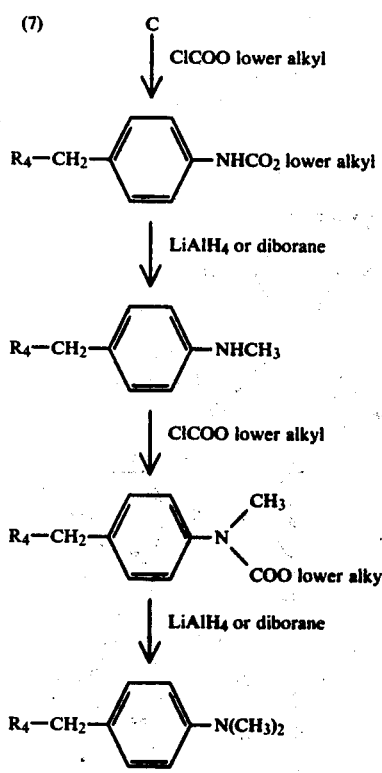
-continued
(8)
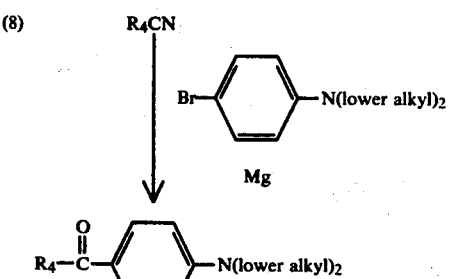
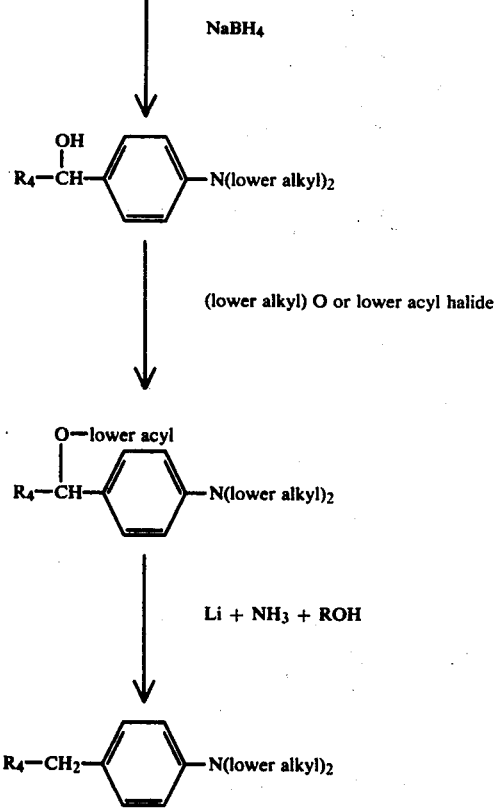

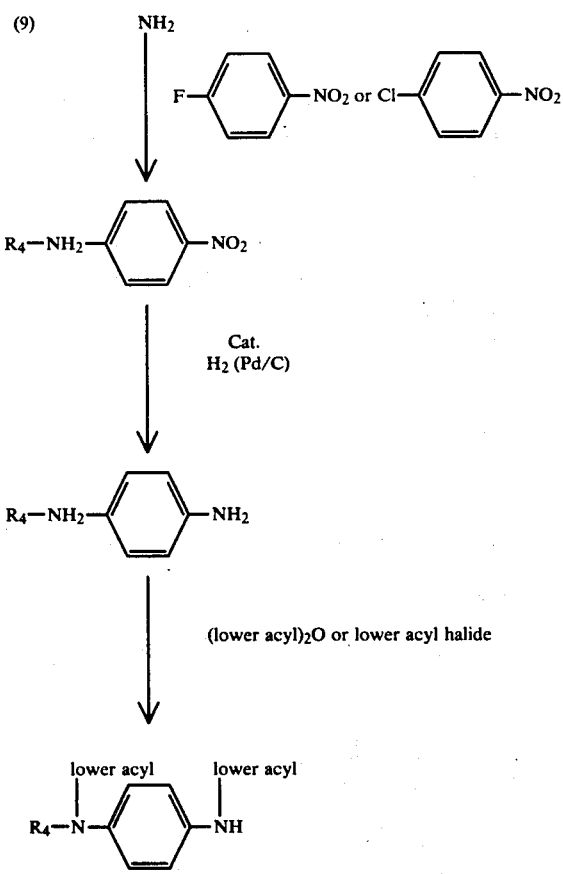
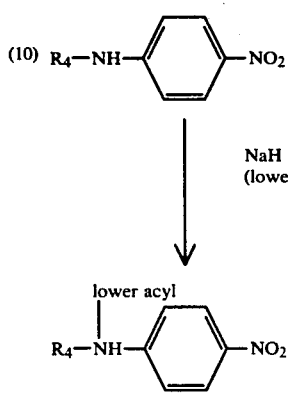
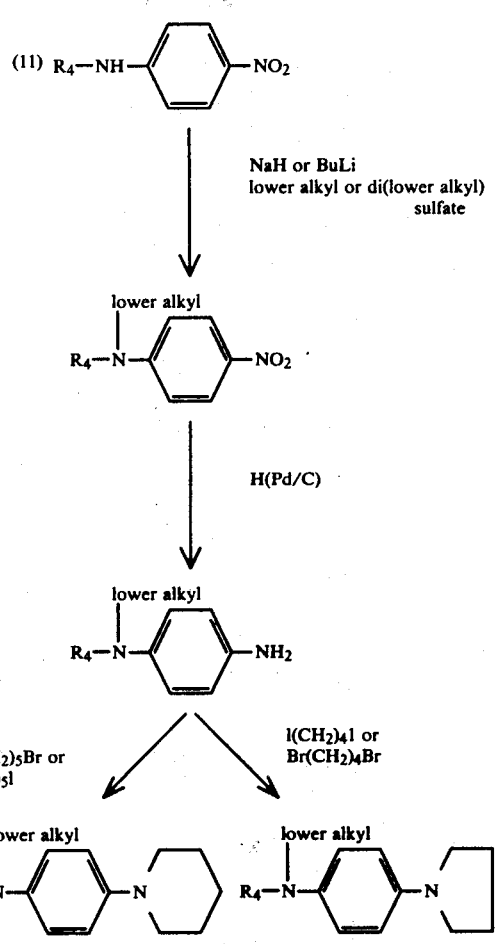
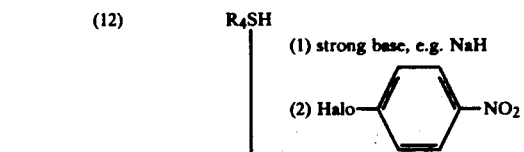
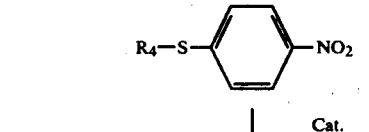
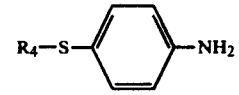
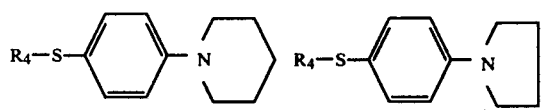

(13) 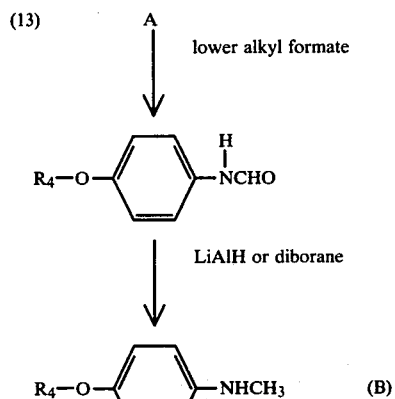
(14) 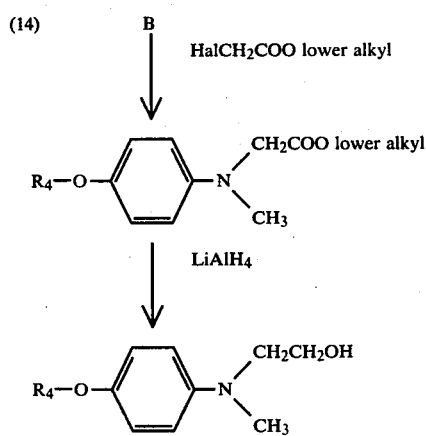
(15) 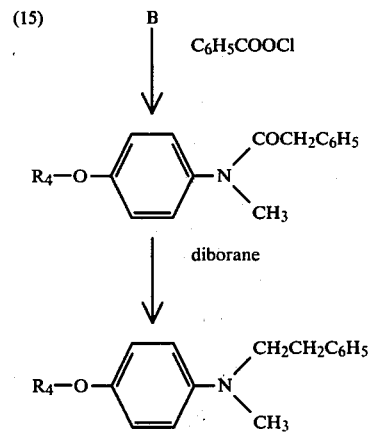
(16) 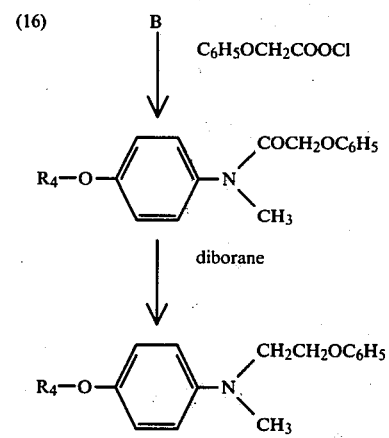
(17) 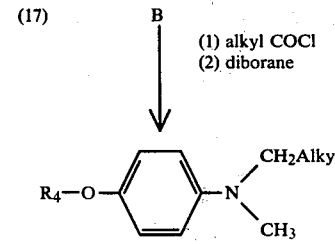

(18) 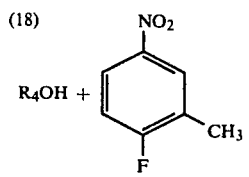
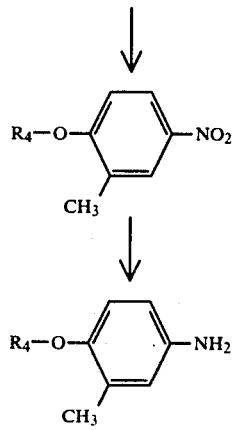
(19) 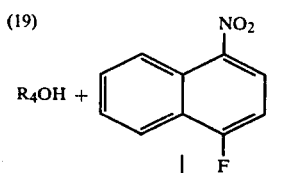
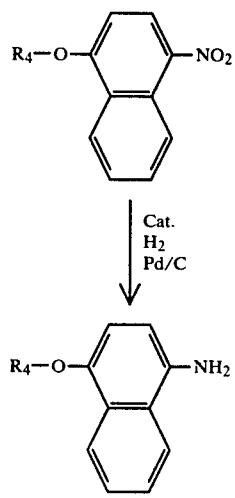
(20) 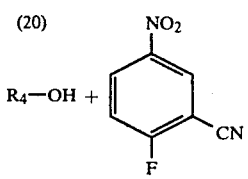
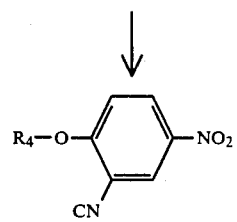
(21) B ↓ 1-chloro-2-pyrrolidino ethane
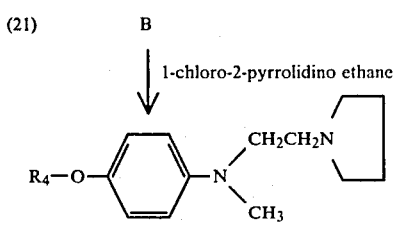
B ↓ 1-chloro-ω-N,N-dimethyl-alkylamine
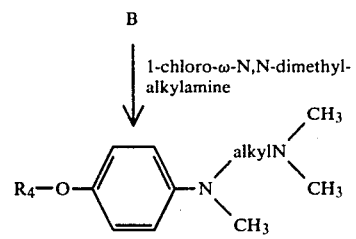

(22)

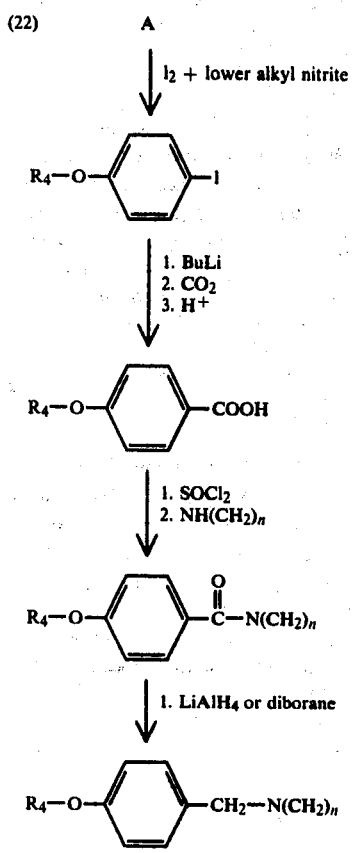

(23)

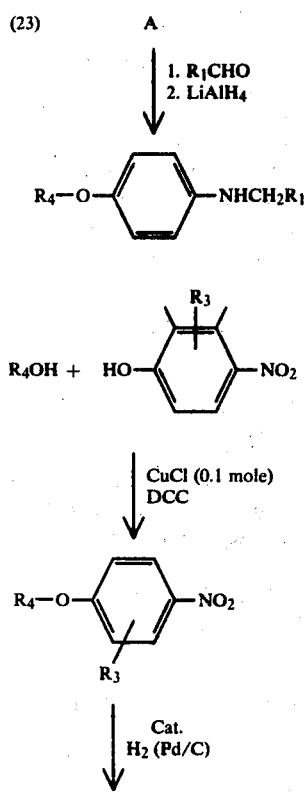

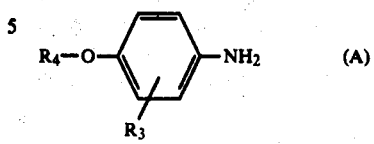

(A)

DETAILED DESCRIPTION OF THE INVENTION

The following examples and tabulated biological data constitute specific embodiments of the invention. In the examples a variety of conventional abbreviations are used. All such expressions are believed to be known to those skilled in the art. The expression "SSB" refers to Skelly-solve B, a commercial mixture of hexane hyrocarbons. "DMF" refers to dimethylformamide. "THF" means tetrahydrofuran. "TLC" means thin layer chromatography. "NMR" means nuclear magnetic resonance. "IR" means infrared. "TFA" refers to trifluoroacetic acid and "HMPA" means hexamethylphosphoramide.

EXAMPLE 1

4-Methoxybicyclo[2,2,2]octan-1-one

Methanol (68 ml.) was added to a flask equipped with a mechanical stirrer, a thermometer and a Dry Ice condenser. Butadiene (dried by passage through a Drierite trap) was then passed into the condenser until 72 ml had been collected. The mixture was then diluted with 280 ml. of methanol and cooled in an ice methanol bath. N,N-Dibromobenzene sulfonamide (64 g.) was added in 10 portions at a rate to keep the temperature at $-12°$ to $-8°$ (15 min. intervals). The reaction mixture was then stirred for 3.5 hrs at room temperature and poured into 800 ml. of water. The precipitated oil was extracted with 4 100 ml. portions of pentane and the extract taken to dryness. The residual oil was distilled at 63 mm to give 43.61 g. of 1-bromo-2-methoxy-3-butane, bp $69°-77°$.

A mixture of 87.7 g. of KOH and 1 l of diethylene glycol in a flask equipped for distillation was stirred at $95°-100°$ until the solid had dissolved. To the hot well stirred mixture there was added over 30 min. 163.7 g. of the bromoether. When the addition was complete the pot temperature was slowly (1° in 3 min.) raised to 130°; the mixture was stirred at this temperature for 15 min. Water (55 ml.) was added and the temperature raised to 145°. After 15 ml. of distillate had been collected at the upper temperature heating was stopped. The aqueous layer was separated from the distillate and the organic layer dried over sodium sulfate. Distillation of this last oil gave 62.68 g. of 2-methoxybutadiene, bp $69°-74°$ (atm).

A mixture of 14.89 g. of 2-methoxybutadiene, 16.95 g. of methyl vinyl ketone, 0.05 g. of hydroquinone and 37 ml. of benzene was heated for 15 hrs at 123° in a glass bomb. Benzene and excess reagents were removed on the rotary evaporator and the residual oil distilled at 8 mm. There was obtained 19.23 g. of 1-Acetyl-4-methoxy-3-cyclohexene, bp $100°-104°$.

A mixture of 13.2 g. of p-toluenesulfonic acid and 0.9 g. of hydroquinone in 540 ml. of benzene was heated at reflux under a Dean Stark trap until no more water was evolved. A solution of 90.6 g. of 1-Acetyl-4-methoxy-3- cyclohexene in 750 ml. of benzene was then added to the refluxing solution over 6 hrs. Following an additional hr's heating the mixture was cooled and treated with 16 ml. of 4.64 N methanolic sodium methoxide. The mixture was washed twice with water and the solvent evaporated in vacuum. The residual oil was distilled at 0.45 mm to afford 64.2 g. of bicyclic ketone 4-Methoxybicyclo[2,2,2]octan-2-one, bp 77°–82°.

EXAMPLE 2

Bicyclo[2,2,2]-1-octanol

4-Methoxybicyclo[2,2,2]octan-2-one (12.0 g.) and 10 ml. of hydrazin hydrate was added to a solution of 14.9 g. of KOH in 230 ml. of diethylene glycol. The mixture was then stirred under reflux for 1 hr. The temperature of the mixture was then raised to 200° by distilling off solvent, the distillate was collected. Following 3 hrs heating at 200° the mixture was cooled and diluted with 1 l of water. The precipitated oil was extracted with ether. The distillate was similarly extracted. The combined extracts were washed in turn with water and brine. The solvent was removed at atmospheric pressure by distillation through a short fractionating column. The residual oil afforded 7.10 g. of product 1-methoxybicyclo[2,2,2]octane as a fragrant liquid, bp 178°–184° (atm).

To an ice cooled solution of 39.6 g. of 1-methoxybicyclo[2,2,2]octane in 112 ml. of acetic anhydride there was added dropwise 3.63 ml. of stannic chloride. Following 2 hrs stirring at room temperature the mixture was poured into water. The precipitated oil was taken up in ether and washed in turn with aqueous $NaHCO_3$, water and brine. The oil which remained when the extract was taken to drynexx was distilled at 15 mm. There was obtained 21.4 g. of foreruns bp 42°–51° and 33.01 g. of acetate 1-acetoxybicyclo[2,2,2]octane bp 90°–97°.

A solution of 5.63 g. of the acetate in 100 ml. of ether was added to a well stirred suspension of 1.34 g. of lithium aluminum hydride in 10 ml. of ether over 25 min. The mixture was heated at reflux for 1.5 hrs and then cooled in ice. Water (2 ml.) and 55 ml. of 2.5 N HCl was then added and the organic layer separated. This solution was washed with water and brine and taken to dryness. The volatile residual solid was recrystallized from ether:pet ether to give 3.0 g. of the alcohol bicyclo[2,2,2]-1-octanol, m.p. 208°–215° (sealed tube).

EXAMPLE 3

1-(p-Nitrophenoxy)-bicyclo[2,2,2]octane

A mixture of 10 g. of [2,2,2]bicyclo-1-octanol and 3.37 g. of 56% sodium hydride in mineral oil in 163 ml. each of benzene and DMF was heated at gentle reflux for 45 min. The mixture was cooled to room temperature and 12.4 g. of p-chloroitrobenzene was added. The mixture was again brought to reflux. Following 15 hrs heating the dark mixture was allowed to cool and washed thoroughly with water and then brine. The residue which remained when the solution was taken to dryness was chromatographed on 1 l. of silica gel. Elution with 20% benzene in Skellysolve B afforded 2.38 g. of recovered chloronitrobenzene; elution with benzene gave crude product and 1:1 benzene ethyl acetate afforded recovered carbinol.

This last fraction was recrystallized from ether:pet ether to yield 5.28 g. of starting material.

The product 1(p-nitrophenoxy)-bicyclo[2,2,2]octane was recrystallized from ether:pet ether to afford 5.97 g. of yellowish crystals, m.p. 91.5°–94°. This analytical sample melted at 92°–94.5°.

Anal. Calcd for $C_{14}H_{17}NO_3$: C, 67.99; H, 6.93. Found: C, 67.81; H, 7.16.

EXAMPLE 4 p-(Bicyclo[2,2,2]oct-1-yloxy)aniline

A mixture of 1.29 g. of 1-(p-nitrophenoxy)-bicyclo[2,2,2]-octane and 0.12 g. of 10% palladium on charcoal in 200 ml. ethyl acetate was shaken under hydrogen. When the uptake of gas ceased (20 min.), the catalyst was removed by filtration and the filtrate taken to dryness. The residual solid was recrystallized from aqueous methanol to give 1.0 g. of the amine, p-(bicyclo[2,2,2]oct-1-yloxy)aniline m.p. 171°–173°.

Anal. Calcd for $C_{14}H_{19}NO$: C, 77.38; H, 8.81; N, 6.45. Found: C, 77.51; H, 8.99; N, 6.59.

EXAMPLE 5

4'-(Bicyclo[2,2,2]oct-1-yloxy)acetanilide

A solution of 3.0 g. of p-(bicyclo[2,2,2]oct-1-yloxy)aniline and 1.5 ml. of acetic anhydride in 50 ml. of THF was allowed to stand at room temperature for 5 hrs. The bulk of the solvent was removed in vacuum and the residue suspended in water. The solid was collected on a filter and recrystallized from aqueous methanol. There was obtained 3.15 g. of the amide, 4'-(bicyclo[2,2,2]oct-1-yloxy)acetanilide m.p. 183°–185°.

The analytical sample melted at 184°–185°.

Anal. Calcd for $C_{16}H_{21}NO_2$: C, 74.10; H, 8.16. Found: C, 74.14; H, 8.52.

EXAMPLE 6 p-(Bicyclo[2,2,2]oct-1-yloxy)-N-ethylaniline Hydrochloride

A solution of 4.99 g. of 4'-(bicyclo[2,2,2]oct-1-yloxy)acetanilide in 100 ml. THF was added dropwise to 1.0 g. of $LiAlH_4$ in 10 ml. of THF. Following 6 hrs heating at reflux the mixture was cooled in ice and treated in turn with 1 ml. each of $H_2O$ and 15% NaOH and 3 ml. $H_2O$. The precipitated gel was removed by filtration. The filtrate was taken to dryness, the residue dissolved in 25 ml. of ether and this solution treated with 25 ml. of 3.7 N ethereal HCl. The precipitated solid was recrystallized twice from $CH_2Cl_2$-ethyl acetate to afford 4.35 g. of p-(bicyclo[2,2,2]oct-1-yloxy)-N-ethylaniline Hydrochloride, m.p. 167°–169°.

Anal. Calcd for $C_{16}H_{24}ClNO$: C, 68.19; H, 8.58. Found: C, 67.94; H, 8.53.

EXAMPLE 7

4'-(Bicyclo[2,2,2]oct-1-yloxy)-N-ethylacetanilide

A solution of 3.0 g. of p-(bicyclo[2,2,2]oct-1-yloxy)-N-ethylaniline hydrochloride in $CH_2Cl_2$ was washed with $NaHCO_3$ and taken to dryness. The residue was dissolved in 50 ml. THF and treated with 1.5 ml. of acetic anhydride. At the end of 4 hrs the solvent was removed in vacuum and the residue diluted with water. The precipitated solid was recrystallized from Skellysolve B to afford 2.35 g. of 4'-(bicyclo[2,2,2]oct-1-yloxy)-N-ethylacetanilide, m.p. 99°–101°.

Anal. Calcd for $C_{18}H_{25}NO_2$: C, 75.22; H, 8.77. Found: C, 75.31; H, 8.82.

EXAMPLE 8 p-(Bicyclo[2,2,2]oct-1-yloxy)-N,N-diethylaniline Hydrochloride

4'-(Bicyclo[2,2,2]-oct-1-yloxy)-N-ethylacetanilide (3.59 g.) was reduced with LiAlH$_4$ (0.80 g.) and the product worked up exactly as above. The crude free base was chromatographed over 200 ml. of silica gel (elution with NH$_3$ saturated benzene followed by NH$_3$ saturated 1:1 benzene:CHCl$_3$). The fractions which were pure by TLC were combined, converted to the HCl salt and recrystallized from acetonitrile. There was obtained 0.81 g. of p-(bicyclo[2,2,2]oct-1-yloxy)-N,N-diethylaniline Hydrochloride, m.p. 234°–237° (dec).

Anal. Calcd for C$_{18}$H$_{28}$ClNO: C, 69.76; H, 9.11. Found: C, 69.89; H, 9.04.

The remaining fraction gave on conversion to the HCl salt 0.66 g. of p-(bicyclo[2,2,2]oct-1-yloxy)-N-ethylaniline hydrochloride, m.p. 167°–169°.

EXAMPLE 9

N-Benzyl-p(bicyclo[2,2,2]oct-1-yloxy)aniline

A solution of 9.70 g. of p-(bicyclo[2,2,2]oct-1-yloxy)aniline and 4.70 g. of benzaldehyde in 250 ml. of benzene was heated at reflux under a Deane-Stark trap for 8 hrs. The solution was taken to dryness to leave behind 14.42 g. of solid, m.p. 148°–156°.

A solution of 14.18 g. of the Shiff base in 250 ml. of THF was added to a suspension of 7.0 g. of LiAlH$_4$ in 75 ml. of THF. The mixture was stirred at room temperature for 1 hour and treated in turn with 7 ml. H$_2$O, 7 ml. 15% NaOH and 21 ml. H$_2$O. The precipitated gel was collected on a filter and washed well with CH$_2$Cl$_2$. The combined filtrates were taken to dryness and recrystallized from CH$_2$Cl$_2$:methanol to afford 12.33 g. of N-benzyl-p(bicyclo[2,2,2]oct-1-yloxy)aniline, m.p. 155°–157°.

Anal. Calcd for C$_{21}$H$_{25}$NO: C, 82.04; H, 8.20. Found: C, 81.33; H, 8.57.

EXAMPLE 10

N-(p-[2,2,2-bicyclooctyloxy]phenyl)pyrrolidine

A mixture of 2.17 g. of the 4'-(bicyclo[2,2,2]oct-1-yloxy)aniline, 2.8 g. K$_2$CO$_3$ and 2.18 g. (1.2 ml.) of Br(CH$_2$)$_4$Br in 25 ml. EtOH was heated at reflux for 20 hr. The mixture was diluted with H$_2$O and this extracted with Et$_2$O. The organic layer was washed with H$_2$O and brine and taken to dryness. The residual solid was recrystallized several times from MeOH to give 1.63 g. of N-(p-[2,2,2-bicyclooctyloxy]phenyl)pyrrolidine, m.p. 99°–100°.

Anal. Calcd for C$_{18}$H$_{25}$NO: C, 79.66; H, 9.29; N, 5.16. Found: C, 79.47; H, 9.31; N, 4.82.

EXAMPLE 11

1-[p-(Bicyclo[2,2,2]oct-1-yloxy)phenyl]piperidine

A mixture of 2.17 g. of 4'-(bicyclo[2,2,2]oct-1-yloxy)aniline, 3.25 g. of 1,5-diiodopentane and 2.8 g. of K$_2$CO$_3$ was stirred under reflux for 2 hrs. The mixture was then poured into water and extracted with methylene chloride. The residue which remained when the solution was taken to dryness was chromatographed on 250 ml. of silica gel (elution with NH$_3$ saturated benzene). The crystalline fractions were combined and recrystallized twice from petroleum ether (cooling in freezer), to give 0.85 g. of 1-[p-(bicyclo[2,2,2]oct-1-yloxy)phenyl]piperidine, m.p. 66°–68°.

Anal. Calcd for C$_{19}$H$_{27}$NO: C, 79.95; H, 9.54. Found: C, 80.16; H, 9.65.

EXAMPLE 12

N-Carbethoxy-4-(2,2,2-bicyclooctyloxy)aniline

To an ice cooled solution of 5.0 g. of 4'-(bicyclo[2,2,2]oct-1-yloxy)aniline in 25 ml. pyridine there was added dropwise 4.4 ml. of C$_2$H$_5$O$_2$CCl. Following 5 hr standing in the cold the mixture was diluted to 200 ml. with ice:H$_2$O. The precipitated solid, N-carboethoxy-4-(2,2,2-bicyclooctyloxy)aniline, was recrystallized from MeOH to a constant m.p. of 126.5°–127.5° (5.82 g.).

Anal. Calcd for C$_{17}$H$_{23}$NO$_3$: C, 70.56; H, 8.01; N, 4.84. Found: C, 70.91; H, 8.20; N, 4.45.

EXAMPLE 13

N-Methyl-4-(2,2,2-bicyclooctyloxy)aniline hydrochloride

A solution of 6.01 g. of N-carbethoxy-4-(2,2,2-bicyclooctyloxy)aniline in 110 ml. THF was added to 0.80 g. LiAlH$_4$ in 8 ml. of THF. The mixture was stirred at reflux for 5 hr and then cooled in ice. There was then added in turn 0.8 ml. H$_2$O, 0.8 ml. 15% NaOH and 2.4 ml. H$_2$O. The precipitated salts were collected on a filter and the filtrate taken to dryness. The residual oil was dissolved in 25 ml. Et$_2$O and treated with 2.3 ml. 6.4 N HCl in Et$_2$O. The precipitate was recrystallized from CH$_2$Cl$_2$: EtOAc to afford 1.91 g. of N-methyl-4-(2,2,2-bicyclooctyloxy)aniline hydrochloride, m.p. 210°–215°.

Anal. Calcd for C$_{15}$H$_{22}$ClNO: C, 67.27; H, 8.28; N, 5.23. Found: C, 66.85; H, 8.32: N: 5.18.

EXAMPLE 14

N-Methyl, N-carbethoxy-4-(2,2,2-bicyclooctyloxy)aniline

A solution of 3.08 g. of N-methyl-4-(2,2,2-bicyclooctyloxy)aniline hydrochloride in CH$_2$Cl$_2$ was washed with NNaOH and then taken to dryness. To an ice cooled solution of the residue in 25 ml. pyridine there was added dropwise 2.2 ml. of ClCO$_2$C$_2$H$_5$. Following 18 hour standing in the cold, the mixture was poured into ice:H$_2$O. The precipitated oil was extracted with Et$_2$O and this extract washed in turn with H$_2$O, 2.5 N HCl, H$_2$O, NaHCO$_3$ and finally brine. The mixture was taken to dryness to afford N-methyl, N-carbethoxy-4-(2,2,2-bicyclooctyloxy)aniline as a gum.

EXAMPLE 15

N,N-Dimethyl-4-(2,2,2-bicyclooctyloxy)aniline

A solution of the crude N-methyl, N-carbethoxy-4-(2,2,2-bicyclooctyloxy)aniline in 30 ml. THF was added to 0.36 g. LiAlH$_4$ in 4 ml. THF. Following 5.5 hour heating at reflux the mixture was cooled in ice and treated in turn with 0.36 ml. H$_2$O, 0.36 ml. 15% NaOH and 1.1 ml. H$_2$O. The inorganic gel was collected on a filter and the filtrate taken to dryness. The residual oil was chromatographed on 100 ml. silica gel (elution with C$_6$H$_6$ saturated with NH$_4$OH, then 1:1 C$_6$H$_6$:CHCl$_3$ saturated with NH$_4$OH. Those fractions which were similar by TLC were combined and converted to the HCl salt. There was obtained solid N,N-dimethyl-4-(2,2,2-bicyclooctyloxy)aniline m.p. 203°–208°.

Anal. Calcd for $C_{16}H_{24}ClNO \cdot \frac{1}{2} H_2O$: C, 66.07; H, 8.66; N, 4.82. Found: C, 66.40; H, 8.20; N, 5.46.

EXAMPLE 16 p-(1-Adamantyloxy)nitrobenzene

A solution of 1-adamantanol in 40 ml. DMF and 80 ml. $C_6H_6$ was treated with 1.38 g. NaH (56% in mineral oil) and heated at reflux for 30 min. The mixture was cooled, treated with 4.65 g. p-fluoronitrobenzene and then heated at reflux for 6 hours. The mixture was allowed to cool, washed well with $H_2O$ and then brine and taken to dryness. The residue was chromatographed on 1 l. silica gel (elution with 1:1 $C_6H_6$:SSB) and the crystalline fractions combined. This was recrystallized from SSB to give 5.33 g. of p-(1-adamantyloxy)-nitrobenzene, m.p. 132.5°–134°.

EXAMPLE 17 p-(1-Adamantyloxy)aniline

A suspension of 2.28 g. 10% Pd/C in a solution of 22.8 g. of p-(1-adamantyloxy)nitrobenzene in 150 ml. EtOAc was shaken under $H_2$ until the theoretical amount of $H_2$ was taken up. The catalyst was removed on a filter and the filtrate taken to dryness. The residue was recrystallized from MeOH to give 14.22 g. of p-(1-adamantyloxy)aniline, m.p. 172.5°–175°.

EXAMPLE 18 p-(1-Adamantyloxy)acetanilide

A solution of 5.0 g. of p-(1-adamantyloxy)aniline and 2.2 ml. of acetic anhydride in 100 ml. of THF was allowed to stand overnight at room temperature. The solution was then taken to dryness in vacuum. The residual solid was recrystallized from aqueous methanol to yield 5.50 g. of the amide, p-(1-adamantyloxy)acetanilide m.p. 167°–169°.

Anal. Calcd for $C_{18}H_{23}NO_2$: C, 75.75; H, 8.12. Found: C, 75.29; H, 8.14.

EXAMPLE 19

N-Carbethoxy-4-(1-adamantyloxy)aniline

To an ice cooled solution of 5.0 g. of p-(1-adamantyloxy)aniline in 50 ml. pyridine, there was added dropwise 3.95 ml. $ClCO_2C_2H_5$. Following 18 hours standing in the cold the mixture was poured onto ice:$H_2O$. The solid was collected on a filter and recrystallized from MeOH to give 3.98 g. of solid N-carbethoxy-4-(1-adamantyloxy)aniline, m.p. 116.5°–118°. There was also obtained a second crop of 1.63 g., m.p. 116.5°–118°.

Anal. Calcd for $C_{19}H_{25}NO_3$: C, 72.35; H, 7.99; N, 4.44. Found: C, 72.40; H, 7.90; N, 4.17.

EXAMPLE 20

N-Methyl-4-(1-adamantyloxy)aniline hydrochloride

A solution of 5.61 g. of N-carbethoxy-4-(1-adamantyloxy)aniline in 100 ml. THF was added dropwise to 0.90 g. $LiAlH_4$ in 10 ml. THF. Following 5 hours heating at reflux the mixture was cooled in ice and treated in turn with 0.9 ml. $H_2O$, 0.9 ml. 15% NaOH and 2.7 ml. $H_2O$. The precipitate was sequestered on a filter and the filtrate taken to dryness. The residue was dissolved in ether and this treated with an excess 6.4 N HCl in $Et_2O$. The solid was recrystallized from $CH_2Cl_2$:EtOAc to give 3.32 g. of N-methyl-4-(1-adamantyloxy)aniline hydrochloride, m.p. 207.5°–208.5°.

Anal. Calcd for $C_{17}H_{24}ClNO$: C, 69.49; H, 8.23; N, 4.77. Found: C, 69.19; H, 8.23; N, 4.83.

EXAMPLE 21

N-Methyl, N-Carbethoxy-4-(1-adamantyloxy)aniline

A solution of the free base from 2.82 g. of the N-methyl-4-(1-adamantyloxy)aniline hydrochloride in 20 ml. pyridine was treated dropwise with 1.64 ml. $ClCO_2C_2H_5$. Following 18 hours standing in the cold the mixture was poured into ice:$H_2O$. This was extracted with $Et_2O$ and the organic layer washed in turn with $H_2O$, cold 2.5 N HCl, $H_2O$ NaHCO$_3$ and brine. The extract was then taken to dryness to leave behind N-methyl, N-carbethoxy-4-(1-adamantyloxy)aniline as an oil.

EXAMPLE 22

N,N-Dimethyl-4-(1-adamantyloxy)aniline hydrochloride hydrate

A solution of N-methyl, N-carbethoxy-4-(1-adamantyloxy)aniline in 50 ml. THF was added to 0.43 g. $LiAlH_4$ in 5 ml. THF. Following 6 hours hearing at reflux the mixture was cooled in ice and treated with 0.4 ml. $H_2O$, 0.4 ml. 15% and 1.2 ml. $H_2O$. The inorganic gel was removed on a filter and the filtrate taken to dryness. The residue in $Et_2O$ was treated with an excess of 6.4 N HCl in $Et_2O$. The solid was recrystallized from $CH_2Cl_2$:EtOAc to give the N,N-dimethyl-4-(1-adamantyloxy)aniline hydrochloride m.p. 214°–216°.

Anal. Calcd for $C_{18}H_{26}NOCl \cdot \frac{1}{2} H_2O$: C, 68.24; H, 8.54; N, 4.42. Found: C, 67.91; H, 8.28; N, 4.55.

EXAMPLE 23

4-(1-Adamantyloxy)acetanilide

A mixture of 5.0 g. of p-(1-adamantyloxy)aniline and 2.65 ml. $Ac_2O$ in 60 ml. THF was allowed to stand overnight. The bulk of the solvent was then removed in vacuum and the residue diluted with $H_2O$. The precipitated solid was recrystallized from MeOH to give 3.69 g. 4-(1-adamantyloxy)acetanilide, m.p. 167°–168.5°, and a second crop of 1.46 g., m.p. 165°–167°.

Anal. Calcd for $C_{18}H_{23}NO_2$: C, 75.75; H, 8.12; N. 4.91. Found: C, 75.66; H, 8.04; N, 4.78.

EXAMPLE 24

N-Ethyl-4-(1-adamantyloxy)aniline hydrochloride

A solution of 5.15 g. of 4-(1-adamantyloxy)acetanilide in 110 ml. THF was added to 0.94 g. $LiAlH_4$ in 10 ml. THF. The mixture was stirred at reflux for 5 hours, cooled in ice and treated in turn with 0.95 ml. $H_2O$, 0.95 ml. 15% NaOH and 2.8 ml. $H_2O$. The precipitated salts were collected on a filter and the filtrate taken to dryness. The residue was chromatographed on 400 ml. silica gel (elution with $C_6H_6$ saturated with $NH_4OH$). The fractions which were similar by TLC were combined and converted to the hydrochloride. This was recrystallized several times from $CH_2Cl_2$:EtOAc to give 0.45 g. of N-ethyl-4-(1-adamantyloxy)aniline hydrochloride, m.p. 185°–187.5°.

Anal. Calcd for $C_{18}H_{26}NOCl$: C, 70.22; H, 8.51; N, 4.55. Found: C, 70.25; H, 8.46; N, 4.20.

EXAMPLE 25

N-Ethyl-4-(1-adamantyloxy)acetanalide

A solution of the free base from 2.02 g. of N-ethyl-4-(1-adamantyloxy)aniline hydrochloride and 0.7 ml.

Ac₂O in 40 ml. THF was allowed to stand overnight. The bulk of the THF was removed in vacuum and the residue diluted with H₂O. The precipitate was recrystallized from MeOH to give 1.50 g. of amide, N-ethyl-4-(1-adamantyloxy)acetanalide m.p. 112.5°–114.5°.

Anal. Calcd for $C_{20}H_{27}NO_2$: C, 76.64; H, 8.68; N, 4.47. Found: C, 76.67; H, 8.96; N, 4.22.

EXAMPLE 26

N,N-Diethyl-4-(1-adamantyloxy)aniline hydrochloride

A solution of 1.50 g. of N-ethyl-4-(1-adamantyloxy)acetanalide in 30 ml. THF was added to 0.25 g. LiAlH₄ in 3 ml. THF. The mixture was heated at reflux for 6.5 hours, and then cooled in ice. There was added 0.25 ml. H₂O, 0.25 ml. 15% NaOH and 0.75 ml. H₂O. The inorganic gel was collected on a filter and the filtrate taken to dryness. The residue was chromatographed on 150 ml. silica gel (elution with C₆H₆ saturated with NH₄OH). The fractions which were similar by TLC were combined and converted to the hydrochloride. This was recrystallized from CH₃CN to give a small amount of N,N-diethyl-4-(1-adamantyloxy)aniline hydrochloride, m.p. 218°–223°.

EXAMPLE 27

N,(p-[1-adamantyloxy]phenyl)pyrrolidine

A mixture of 2.0 g. of p-(1-adamantyloxy)aniline, 2.37 g. K₂CO₃ and 1.78 g. Br(CH₂)₄Br in 25 ml. EtOH was stirred under reflux for 24 hours. The mixture was then diluted with H₂O and extracted with Et₂O. The organic layer was washed with H₂O and brine and taken to dryness. The residue was recrystallized from MeOH to give 1.07 g. of N,(p-[1-adamantyloxy]phenyl)pyrrolidine, m.p. 120°–122°.

Anal. Calcd for $C_{20}H_{27}NO$: C, 80.76; H, 4.71. Found: C, 81.05; H, 9.16.

EXAMPLE 28

N,-(p-[1-adamantyloxy]phenyl)piperidine

A mixture of 2.0 g. of p-(1-adamantyloxy)aniline, 2.3 g. K₂CO₃, and 1.22 ml. I(CH₂)₅I in 100 ml. EtOH was heated at reflux for 20 hours. The mixture was then diluted with H₂O and extracted with CH₂Cl₂. The organic layer was washed with brine and then taken to dryness. The residue was chromatographed on 200 ml. silica gel (elution with C₆H₆ saturated with NH₄OH). The fractions which were similar by TLC were combined and then recrystallized from pet. ether. There was obtained 0.53 g. of N,-(p-[1-adamantyloxy]phenyl)-piperidine, m.p. 72°–73.5°.

Anal. Calcd for $C_{21}H_{29}NO$: C, 80.98; H, 9.38; N, 4.50 Found: C, 81.10; H, 9.50; N, 4.55.

EXAMPLE 29

1-Benzoyladamantane

A solution of 5.0 g. (0.03 mole) of 1-adamantane carbonitrile in 80 ml. Et₂O was added to 20 ml. 2.85 M C₆H₅MgBr in Et₂O. Following 18 hour stirring at room temperature, the mixture was cooled in ice and treated with 100 ml. 2.5 N HCl in Et₂O, and 500 ml. H₂O. The mixture was then allowed to stir at room temperature for 4 hours. The organic layer was then washed with H₂O, NaHCO₃ and brine and taken to dryness. The residue was recrystallized from a small amount of MeOH to afford 5.80 g. (76%) of the ketone, 1-benzoyladamantane m.p. 48°–50°; $\nu_{max}$ 1680 cm⁻¹.

Anal. Calcd for $C_{17}H_{20}O$: C, 84.95; H, 8.34. Found: C, 84.96; H, 8.39.

EXAMPLE 30

α-[1-Adamantyl]-benzylalcohol

To a warm solution of 5.80 g. (0.024 mole) of 1-benzoyladamantane in 60 ml. 95% iPrOH there was added 1.0 g. NaBH₄. At the end of 5 hours stirring at room temperature the solvent was removed in vacuum. The residue was dissolved in H₂O and Et₂O. The organic layer was washed with H₂O and brine and taken to dryness. The residue was recrystallized from petroleum ether (cooling in freezer) to give 5.04 g. (86%) of the alcohol, α-[1-adamantyl]-benzylalcohol m.p. 52°–53°.

Anal. Calcd for $C_{17}H_{22}O$: C, 84.24; H, 9.15. Found: C, 84.27; H, 9.35.

EXAMPLE 31

1-Benzyladamantane

A solution of 5.04 g. (0.021 mole) of α-[1-adamantyl] benzyl alcohol in 10 ml. Ac₂O and 20 ml. pyridine was allowed to stand at room temperature for 7 hours. The mixture was then poured onto ice:H₂O, and extracted with Et₂O. The extract was then washed in turn with H₂O, 2.5 N HCl, H₂O and brine and taken to dryness. The crude acetate of the starting material (5.60 g.) was obtained as an amorphous gum.

Ammonia (200 ml.) was distilled into a solution of the above acetate product and 7.6 ml. t-BuOH in 50 ml. THF. There was then added 0.56 g. Li metal in two portions; as soon as the last color faded (5 min.), there was added 5 g. NH₄Cl, and the solvent evaporated under a stream of Na. The residue was dissolved in H₂O and Et₂O. The organic layer was washed with H₂O and brine and taken to dryness. There was obtained 4.29 g. (91%) of solid product, 1-benzyladamantane m.p. 41°–42°: NMR and IR consistent with structure. This material could not be satisfactorily recrystallized.

EXAMPLE 32

α-(1-Adamantyl)-p-nitrotoluene and α-(1-adamantyl)-o-nitrotoluene

Nitric acid (6 ml.) was added quickly to an ice cooled suspension of 4.29 g. (0.019 mole) of 1-benzyladamantane in 30 ml. TFA. The mixture was stirred in the cold until all solid had dissolved (3 hours) and then poured into ice:H₂O. The precipitate was extracted with C₆H₆ and this solution washed in turn with H₂O, NaHCO₃ and brine. The solid which remained when the extract was taken to dryness was chromatographed on 500 ml. silica gel (elution with 25% CH₂Cl₂ in SSB). There was obtained first a product, m.p. 68.5°–71.5°, shown by NMR to be the ortho product α-(1-adamantyl)-o-nitrotoluene. This was recrystallized from MeOH to afford 1.71 g. (33%) of solid, m.p. 71°–73°.

Anal. Calcd for $C_{17}H_{21}NO_2$: C, 75.24; H, 7.80; N, 5.16. Found: C, 75.64; H, 7.85; N, 4.82.

There was next eluted the para isomer, α-(1-adamantyl)-p-nitrotoluene m.p. 101°–112°; 1.65 g. (32%).

Found: C, 75.63; H, 7.90; N, 4.98.

EXAMPLE 33

α-1-Adamantyl-p-toluidine Hydrochloride

A mixture of 1.65 g. (0.0061) of α-(1-adamantyl)-p-nitrotoluene and 0.20 g. of 10% Pd/C in 150 ml. EtOAc was shaken under H₂ until the theoretical uptake of gas was absorbed (20 min.). The catalyst was removed on a filter and the filtrate taken to dryness. The residual oil was dissolved in Et$_2$O and this solution treated with HCl in Et$_2$O. The precipitated solid was recrystallized from MeOH: EtOAc to give 1.06 g. (63%) of α-1-adamantyl-p-toluidine hydrochloride, m.p. 250°-253°.

Anal. Calcd for C$_{17}$H$_{24}$ClN: C, 73.49; H, 8.71; N, 5.04. Found: C, 73.12; H, 8.50; N, 5.13.

EXAMPLE 34

α-1-Adamantyl-o-toluidine Hydrochloride

A mixture of 1.71 g. (0.0063 mole) of α-(1-adamantyl)-o-nitrotoluene and 0.20 g. 10% Pd/C in 150 ml. EtOAc was shaken under H$_2$ until the theoretical amount of H$_2$ had been absorbed (40 min.). The catalyst was removed by filtration and the filtrate taken to dryness. A solution of the residue in Et$_2$O was treated with HCl in Et$_2$O. The precipitated solid was recrystallized from MeOH:EtOAc to give 1.01 g. (58%) of α-1-adamantyl-o-toluidine hydrochloride, m.p. 230°-235°.

Anal. Calcd for C$_{17}$H$_{24}$ClN: C, 73.49; H, 8.71; N, 5.04. Found: C, 73.01; H, 8.83; N, 4.83.

EXAMPLE 35

1-(α-1-Adamantyl-p-tolyl)pyrrolidine

A mixture of α-1-adamantyl-p-toluidine prepared from 2.0 g. (0.0072 mole) of the hydrochloride salt, 0.85 ml. 1,4-dibromobutane and 2.01 g. K$_2$CO$_3$ in 20 ml. EtOH was stirred overnight at reflux. The solvent was then removed in vacuum and the residue dissolved in H$_2$O and Et$_2$O. The organic layer was washed with H$_2$O and brine and taken to dryness. The residue was recrystallized from EtOH to give 1.35 g. (64%) of 1-(α-1-adamantyl-p-tolyl)pyrrolidine, m.p. 147°-148.5°.

Anal. Calcd for C$_{21}$H$_{29}$N: C, 85.36; H, 9.89; N, 4.74. Found: C, 85.73; H, 10.30; N, 4.56.

In a similar manner, using 1,5-diiodopentane, 1-(α-1-adamantyl-p-tolyl)piperidine can be prepared.

EXAMPLE 36

1-(α-1-Adamantyl-o-tolyl)pyrrolidine Hydrochloride

A mixture of α-1-adamantyl-o-toluidine, prepared from 1.85 g. (0.0067 mole) of the hydrochloride salt, 0.80 ml. of 1,4-dibromobutane and 1.86 g. K$_2$CO$_3$ in 20 ml. EtOH was heated at reflux overnight. The bulk of the solvent was removed in vacuum and the residue dissolved in H$_2$O and Et$_2$O. The organic layer was washed with H$_2$O and brine and taken to dryness. The oily residue was chromatographed on 200 ml. silica gel (elution with 30% CH$_2$Cl$_2$ in SSB saturated with NH$_4$OH). The oily fractions which were similar by TLC were combined and dissolved in Et$_2$O. The solid obtained on adding HCl in Et$_2$O was recrystallized from CH$_2$Cl$_2$:EtOAc to yield 0.75 g. (32%) of 1-(α-1-adamantyl-o-tolyl)pyrrolidine hydrochloride, m.p. 188°-191°.

Anal. Calcd fior C$_{21}$H$_{30}$ClNO: C, 75.98; H, 9.11; N, 4.22. Found: C, 76.03. H, 9.29; N, 4.12.

EXAMPLE 37

α-1-Adamantyl-p-toluidine, Ethyl Carbamate

To an ice cooled solution of α-1-adamantyl-p-toluidine, prepared from 2.77 g. (0.01 mole) of the hydrochloride salt, and 1.40 ml. Et$_3$N in 50 ml. THF there was added dropwise with stirring 0.95 ml. of ethyl chloroformate. Following 18 hours standing in the cold, the bulk of the solvent was removed in vacuum. The residue was dissolved in Et$_2$O and H$_2$O. The organic layer was washed with H$_2$O and brine and taken to dryness. The residue was recrystallized twice from SSB (cooling in freezer) to give 1.68 g. (54%) of α-1-adamantyl-p-toluidine, ethyl carbamate, m.p. 130°-132°.

Anal. Calcd for C$_{20}$H$_{27}$NO$_2$: C, 76.64; H, 8.68; N, 4.47. Found: C, 76.55; H, 8.65; N, 4.43.

EXAMPLE 38

N-Methyl α-1-Adamantyl-p-toluidine Hydrochloride

A solution of 1.48 g. (0.0047 mole) of α-1-adamantyl-p-toluidine, ethyl carbamate in 60 ml. THF was added to 0.20 g. LiAlH$_4$ in 10 ml. THF. The mixture was stirred at reflux for 7 hours, cooled in ice and treated in turn with 0.2 ml. H$_2$O, 0.2 ml. 15% NaOH and 0.6 ml. H$_2$O. The inorganic gel was collected on a filter and the filtrate taken to dryness. The residue was chromatographed on 200 ml. silica gel (elution with 30% CH$_2$Cl$_2$:SSB saturated with NH$_4$OH). Those fractions which were similar by TLC were combined and dissolved in Et$_2$O. The solid obtained on adding HCl in Et$_2$O was recrystallized from CH$_2$Cl$_2$:EtOAc to give 0.21 g. (15%) of N-methyl α-1-adamantyl-p-toluidine hydrochloride, m.p. 208°-210°.

Anal. Calcd for C$_{18}$H$_{26}$ClN: C, 71.85; H, 9.05; N, 4.66. Found: C, 71.41; H, 9.15; N, 4.22.

EXAMPLE 39

1-Adamantyl-p-(Dimethylamino)phenyl Ketone Hydrochloride

A Grignard reagent was prepared from 6.0 g. of p-bromo-N,N-dimethyl aniline and 0.73 g. Mg in 60 ml. THF. The solution was cooled in ice and treated with 5.0 g. (0.03 mole) of adamantane-1-carbonitrile in 50 ml. THF. Following 17 hours at room temperature, 0.6 ml. H$_2$O was added and the solid collected on a filter. The filtrate was taken to dryness and dissolved in a mixture of 100 ml. 2.5 N HCl and 200 ml. MeOH. At the end of 4 hours stirring (room temperature) the bulk of the MeOH was removed in vacuum. The solid was collected on a filter and recrystallized from MeOH:2.5 N HCl. There was obtained 2.89 g. of 1-adamantyl(p-dimethylamino)phenyl ketone hyrochloride, m.p. 155°-160°; $\nu_{max}$ 2800, 1690 cm$^{-1}$; m/e+ 283.

A satisfactory CHN analysis was not obtained. The identity of the compound was confirmed by its mass spectrum and IR spectrum. The compound showed a molecular ion at 283; and the calculated molecular weight of the free base is 283.

EXAMPLE 40

α-1-Adamantyl-p-dimethylamino Benzyl Alcohol Hydrochloride

A solution of 1-adamantyl-p-(dimethylamino)phenyl ketone, prepared from 2.19 g. (0.0068 mole) of the amine hydrochloride and 0.30 g. NaBH$_4$ in 50 ml. 95% iPrOH was stirred at room temperature for 6 hours. The bulk of the solvent was then removed in vacuum. The residue was suspended in H$_2$O and collected on a filter. A solution of the crude product in Et$_2$O was treated with HCl in Et$_2$O. The precipitated solid was recrystallized from MeOH:EtOAc to give 0.41 g. (19%) of α-1-adamantyl(p-dimethylamino)benzyl alcohol hydrochloride, m.p. 186°-188° (effervesc.).

Anal. Calcd for C$_{19}$H$_{28}$ClNO: C, 70.89; H, 8.77; N, 4.35. Found: C, 70.91; H, 8.70; N, 4.00.

EXAMPLE 41

N(1-Adamantyl)p-nitroaniline

A mixture of 1.51 g. (0.01 mole) of 1-adamantamine, 1.41 g. p-fluoronitrobenzene and 1.38 g. $K_2CO_3$ in 10 ml. HMPA was stirred overnight in an oil bath at 135°. The mixture was allowed to cool, diluted with $H_2O$ and extracted thoroughly with $C_6H_6$. The organic layer was washed in turn with $H_2O$ and brine and taken to dryness. The waxy residue was recrystallized twice from $Me_2CO$:cyclohexane to give 1.82 g. (67%) of N,1-adamantyl-p-nitroaniline, m.p. 188°–189°.

Anal. Calcd for $C_{16}H_{20}N_2O_2$: C, 70.56; H, 7.40; N, 10.29. Found: C, 70.58; H, 7.36; N, 10.21.

EXAMPLE 42

N(1-Adamantyl)p-phenylenediamine

A mixture of 5.0 g. (0.018 mole) of N,1(adamantyl)p-nitroaniline and 0.50 g. 10% Pd/C in 150 ml. EtOAc was shaken under $H_2$ until the theoretical $H_2$ had been absorbed (40 min.). The catalyst was collected on a filter and the filtrate taken to dryness. The residue was recrystallized from $MeOH:H_2O$ to yield 3.91 g. (88%) of N(1-adamantyl)p-phenylenediamine, m.p. 153°–156°.

Anal. Calcd for $C_{16}H_{22}N_2$: C, 79.28; H, 9.15; N, 11.56. Found: C, 78.72; H, 9.16; N, 11.49.

EXAMPLE 43

N(1-Adamantyl)N,N'-p-phenylenebisacetamide

A mixture of 2.86 g. (0.018 mole) of N-1(adamantyl)p-phenylenediamine in 15 ml. $Ac_2O$ and 30 ml. pyridine was allowed to stand at room temperature for 4 hours. The solution was then poured into ice:$H_2O$ and the precipitate collected on a filter. The residue was recrystallized from $Me_2CO$:cyclohexane to give 1.90 g. (32%) of N(1-adamantyl)N,N'-p-phenylenebisacetamide, m.p. 238°–242°. The analytical sample melted at 245°–246°.

Anal. Calcd for $C_{20}H_{26}N_2O_2$: C, 73.58; H, 8.03; N, 8.58. Found: C, 73.48; H, 8.02; N, 8.72.

EXAMPLE 44

N(1-Adamantyl)4'-nitroacetanilide

Sodium hydride (0.46 g. of 56% dispersion) was added to a solution of 2.94 g. (0.0108 mole) of N(1-adamantyl)p-nitroaniline in 10 ml. DMF and 40 ml. $C_6H_6$. Following 2.5 hours heating at reflux, the mixture was allowed to cool and treated with 1.5 ml. $Ac_2O$. At the end of an additional 1 hour heating the mixture was allowed to cool and washed well with $H_2O$. The residue was chromatographed on 400 ml. silica gel (elution with 20% $Me_2CO:CH_2Cl_2$). There was obtained a first fraction of 1.46 g. recovered starting material followed then by product. This latter was recrystallized from $Me_2CO$:cyclohexane to give 0.83 g. (49% based on starting material consumed) of N(1-adamantyl)4'-nitroacetanilide, m.p. 164°–167°, m/e 314.

Anal. Calcd for $C_{18}H_{22}N_2O_3$: C, 68.76; H, 7.06; N, 8.91. Found: C, 68.02; H, 7.09; N, 8.35.

EXAMPLE 45

N(1-Adamantyl)N-methyl-p-nitroaniline

To a solution of 4.08 g. (0.015 mole) of N(1-adamantyl)p-nitroaniline in 15 ml. DMF and 60 ml. $C_6H_6$ there was added 0.63 of 56% NaH. Following 3 hours stirring at reflux, 10 ml. of $CH_3I$ was added; at the end of an additional 2 hours, 5 ml. $CH_3I$ was added and the mixture heated 2 hours more. The reaction was then diluted with $C_6H_6$ and washed well with $H_2O$. The residue was chromatographed on 600 ml. silica gel (elution with 10% $Me_2CO$ in SSB). The fractions containing product were combined and recrystallized from pet ether (cooling in freezer) to yield 3.31 g. (77%) of solid N(1-adamantyl)N-methyl-p-nitroaniline, m.p. 60°–61° (S. 55°).

Anal. Calcd for $C_{17}H_{22}N_2O_2$: C, 71.30; H, 7.75; N, 9.78. Found: C, 71.37; H, 7.73; N, 9.67.

EXAMPLE 46

N(1-Adamantyl)N-methyl-p-phenylenediamine bis Hydrochloride

A mixture of 3.31 g. (0.0116 mole) of N-1-adamantyl-N-methyl-p-nitroaniline and 0.50 g. 10% Pd/C in 150 ml. EtOAc was shaken under $H_2$ until the theoretical $H_2$ had been taken up. The catalyst was then collected on a filter and the filtrate taken to dryness. A solution of the residue in MeOH was treated with 50 ml. 5 N HCl in $Et_2O$. The solid which remained when this last was taken to dryness was recrystallized from MeOH:EtOAc. There was obtained 3.43 g. (88%) of N(1-adamantyl)N-methyl-p-phenylenediamine bis hydrochloride, m.p. 228°–230°.

Anal. Calcd for $C_{17}H_{26}Cl_2N_2.\frac{1}{2} H_2O$: C, 60.35; H, 8.05; N, 8.28. Found: C, 60.46; H, 7.96; N, 8.39.

EXAMPLE 47

N-Methyl-N-[(p-1-pyrroldinyl)phenyl]-1-adamantanamine

A mixture of N-1-adamantyl-N-methyl-p-phenylenediamine, prepared from 2.43 g. (0.0072 mole) of the bishydrochloride, 0.85 ml. of 1,4-dibromobutane and 2.0 g $K_2CO_3$ in 20 ml. EtOH was heated at reflux overnight. The bulk of the solvent was removed in vacuum. The residue was suspended in $H_2O$ and the solid collected on a filter. This was recrystallized from MeOH to give 1.47 g. (66%) of N-methyl-N-[(p-1-pyrrolidinyl)phenyl]-1-adamantanamine, m.p. 128°–129.5°.

Anal. Calcd for $C_{21}H_{30}N_2$: C, 81.23; H, 9.74; N, 9.03. Found: C, 81.11; H, 9.92; N, 8.88.

In a similar manner, using 1,5-diiodopentane, N-methyl-N-[(p-1-piperidinyl)phenyl]-1-adamantanamine is produced.

EXAMPLE 48 p(1-Adamantylthio)nitrobenzene

To a solution of 5.85 g. (0.035 mole) of 1-adamantanethiol in 40 ml. DMF and 80 ml. $C_6H_6$ there was added 1.46 g. of 56% NaH dispersion. The mixture was heated for 15 minutes and then cooled. Following the addition of 4.91 g. of p-fluoronitrobenzene the mixture was heated at reflux for 5 hours, allowed to cool and then washed well with $H_2O$. The solid which remained when the organic layer was taken to dryness was recrystallized in turn from cyclohexane and $CH_2Cl_2$:cyclohexane. There was obtained 7.38 g. (73%) of p(1-adamantylthio)nitrobenzene, m.p. 145°–147°; m/e 289.

Anal. Calcd for $C_{16}H_{19}NO_2S$: C, 66.40; H, 6.62; N, 4.84. Found: C, 66.36; H, 6.45; N, 4.90.

EXAMPLE 49 p(1-Adamantylthio)aniline

A mixture of 2.89 g. (0.010 mole) of p(1-adamantyl)thionitrobenzene and 0.30 g. of 10% Pd/C in 150 ml. EtOAc was shaken under $H_2$. At the end of 7 hours an additional 0.3 g. of catalyst was added. Following 18 hours reaction time the catalyst was collected on a filter and the filtrate taken to dryness. The residue was recrystallized from MeOH:$H_2O$ to give 2.07 g. (80%) of p(1-adamantylthio)aniline, m.p. 148°–151°.

Anal. Calcd for $C_{16}H_{21}NS$: C, 74.08; H, 8.16; N, 5.40. Found: C, 73.93; H, 8.19; N, 5.46.

EXAMPLE 50

1-(p-1-Adamantylthiophenyl)pyrrolidine

A mixture of 1.47 g. (0.0057 mole) of p-1(adamantylthio)aniline, 1.22 g. of 1,4-dibromobutane and 1.57 g. $K_2CO_3$ in 15 ml. EtOH was heated at reflux overnight. The bulk of the solvent was then removed in vacuum and the residue dissolved in $H_2O$ and $CH_2Cl_2$. The organic layer was washed with $H_2O$ and brine and taken to dryness. The residue was chromatographed on 200 ml. silica gel (elution with 5% $Me_2CO$:SSB). The crystalline fractions were combined and recrystallized from SSB to give 0.88 g. (49%) of 1-(p-1-adamantylthiophenyl)pyrrolidine, m.p. 159°–162°.

Anal. Calcd for $C_{20}H_{27}NS$: C, 76.62; H, 8.68; N, 4.47. Found: C, 76.82; H, 8.57; N, 4.28.

In a similar manner, using 1,5-diiodopentane, 1-(p-1-adamantylthiophenyl)piperidine can be prepared.

EXAMPLE 51

N-Formyl-p-(1-adamantyloxy)aniline

A suspension of 10.0 g. (0.041 mole) of p-(1-adamantyloxy)aniline in 60 ml. ethyl formate was stirred at reflux for 48 hours. The mixture was then taken to dryness and the residue recrystallized from $Me_2CO$:cyclohexane. There was obtained 9.67 g. (87%) of the amide, N-formyl-p-(1-adamantyloxy)aniline m.p. 149°–150°.

Anal. Calcd for $C_{17}H_{21}NO_2$: C, 75.24; H, 7.80; N, 5.16. Found: C, 75.35; H, 7.89; N, 5.22.

EXAMPLE 52

N-Methyl-p-(1-adamantyloxy)aniline

To a stirred suspension of 1.30 g. $LiAlH_4$ in 20 ml. THF there was added 9.17 g. (0.034 mole) of N-formyl-p-(1-adamantyloxy)aniline in 200 ml. THF. Following 8 hours heating at reflux the mixture was cooled in ice and treated in turn with 1.3 ml. each of $H_2O$ and 15% NaOH and 4.9 ml. $H_2O$. The inorganic gel was removed on a filter and the filtrate taken to dryness. The residue was recrystallized from $Me_2CO$:SSB to give 5.96 g. (79%) of amine, N-methyl-p(1-adamantyloxy)aniline m.p. 134°–136°.

EXAMPLE 53

N-(2-Butynyl)-N-methyl-p-(1-adamantyloxy)aniline

A mixture of 2.0 g. (0.0079 mole) of N-methyl-p-(1-adamantyloxy)aniline, 1.07 g. $K_2CO_3$ and 1.03 g. of 1-bromo-2-butyne in 10 ml. DMF and 40 ml. $C_6H_6$ was heated at reflux for 17 hours. The mixture was allowed to cool and washed well with $H_2O$ and brine. The gum which remained when the organic layer was taken to dryness was dissolved in $Et_2O$. The solid which precipitated on addition of HCl in $Et_2O$ was recrystallized from $CH_2Cl_2$:EtOAc. There was obtained 2.09 g. (77%) of N-(2-butynyl)-N-methyl-p-(1-adamantyloxy)aniline, m.p. 180°–181°.

Anal. Calcd for $C_{21}H_{28}ClNO$: C, 73.12; H, 7.89; N, 4.06. Found: C, 73.10; H, 8.23; N, 3.07.

EXAMPLE 54

N-(2-Hydroxyethyl)-N-methyl-p-(1-adamantyloxy)aniline

A mixture of 4.0 g. (0.0016 mole) of N-methyl-p-(1-adamantyloxy)aniline, 2.14 g. $K_2CO_3$ and 1.72 g. ethyl bromoacetate in 20 ml. DMF and 40 ml. $C_6H_6$ was heated at reflux for 17 hours. The mixture was then allowed to cool, washed thoroughly with $H_2O$ and brine and taken to dryness to afford the ester as an amorphous gum. (The NMR is in consonance with the structure).

The crude ester obtained above in 100 ml. THF was added to 1.0 g. $LiAlH_4$ in 20 ml. THF. Following 6 hours heating at reflux, the mixture was cooled in ice and treated in turn with 1 ml. $H_2O$, 1 ml. 15% NaOH and 3 ml. $H_2O$. The inorganic gel was collected on a filter and the filtrate taken to dryness. The residual solid was recrystallized from $Me_2CO$:SSB to give 3.84 g. (80%) of N-(2-hydroxyethyl)-N-methyl-p-(1-adamantyloxy)aniline, m.p. 94°–99°.

Anal. Calcd for $C_{19}H_{27}NO_2$: C, 75.70; H, 9.03; N, 4.65. Found: C, 75.80; H, 9.12; N, 4.44.

EXAMPLE 55

4'-(1-Adamantyloxy)-N-methyl-2-phenylacetanilide

To an ice cooled solution of 2.0 g. (0.0078 mole) of N-methyl-p-(1-adamantyloxy)aniline and 1.08 ml. $Et_3N$ in 40 ml. THF there was added dropwise 1.20 g. phenylacetyl chloride in 20 ml. THF. The mixture was stirred in the cold for 30 min., at room temperature for 4 hours and taken to dryness. The residue was taken up in $Et_2O$ and $H_2O$. The organic layer was washed with $H_2O$ and brine. The residue was recrystallized from SSB (cooling in freezer) to give 2.35 g. (79%) of 4'-(1-adamantyloxy)-N-methyl-2-phenylacetanilide, m.p. 89°–91°.

Anal. Calcd for $C_{25}H_{29}NO_2$: C, 79.96; H, 7.78; N, 3.73. Found: C, 80.17; H, 7.97; N, 3.49.

EXAMPLE 56

4'-(1-Adamantyloxy)-N-methyl-2-phenoxyacetanilide

To an ice cooled solution of 2.0 g. (0.0078 mole) of N-methyl-p-(1-adamantyloxy)aniline and 1.08 g. $Et_3N$ in 40 ml. THF there was added dropwise 1.33 g. phenoxyacetyl chloride. Following 3 hours stirring at room temperature the solvent was removed in vacuum. The residue was treated with $H_2O$ and the solid collected on a filter. This was recrystallized from SSB to afford 2.77 g. (91%) of 4'-(1-adamantyloxy)-N-methyl-2-phenoxyacetanilide, m.p. 89°–91°.

Anal. Calcd for $C_{25}H_{29}NO_3$: C, 76.69; H, 7.47; N, 3.58. Found: C, 76.51; H, 7.48; N, 3.45.

EXAMPLE 57

N-Methyl-N-($\beta$-phenylethyl)-p-(1-adamantyloxy)aniline Hydrochloride

To an ice cold solution of 1.80 g. (0.0048 mole) of N-methyl-p-(1-adamantyloxy)phenylacetanilide in 20 ml. THF there was added 10 ml. N $B_2H_6$ in THF. Following 18 hours standing in the cold, there was added 1 ml. $H_2O$. The bulk of the solvent was removed in vacuum and the residue stirred for 5 hours with 40 ml. 2.5 N HCl. This mixture was then made strongly basic and extracted with $Et_2O$. The extract was washed with $H_2O$ and brine and taken to dryness. The residue, in a small amount of $Et_2O$ was treated with HCl in $Et_2O$. The precipitate was recrystallized from $CH_2Cl_2$:EtOAc to give 1.24 g. (65%) of N-methyl-N-($\beta$-phenylethyl)-p-(1-adamantyloxy)aniline hydrochloride, m.p. 213°–214°.

Anal. Calcd for $C_{25}H_{32}ClNO$: C, 75.44; H, 8.11; N, 3.52; Cl, 8.91. Found: C, 75.02; H, 7.85; N, 3.47; Cl, 9.07.

EXAMPLE 58

N-Methyl-N-($\beta$-phenoxyethyl)-p-(1-adamantyloxy)aniline Hydrochloride

To an ice cold solution of 1.36 g. (0.0035 mole) of N-methyl-p-(1-adamantyloxy)phenoxyacetanilide in 20 ml. THF there was added 7 ml. N $B_2H_6$ in THF. Following 17 hours standing in the cold, 1 ml. $H_2O$ was cautiously added. The bulk of the solvent was removed in vacuum and the residue stirred for 2 hours with 50 ml. 2.5 N HCl. The aqueous layer was then made strongly basic and extracted with $CH_2Cl_2$. This last was washed with $H_2O$ and brine and taken to dryness. The residue was recrystallized from MeOH to give 1.00 g. (76%) of N-methyl-N-($\beta$-phenoxyethyl)p-(1-adamantyloxy)aniline hydrochloride, m.p. 108°–109°.

Anal. Calcd for $C_{25}H_{31}NO_2$: C, 79.53; H, 8.28; N, 3.71. Found: C, 79.26; H, 8.38; N, 3.58.

EXAMPLE 59

N-Methyl-N-(n-octyl)-p-(1-adamantyloxy)aniline Hydrochloride

To an ice cold stirred mixture of 2.80 g. (0.011 mole) of N-methyl-p-(1-adamantyloxy)aniline and 1.51 g. $Et_3N$ in 60 ml. THF there was added 1.77 g. of n-octanoyl chloride in 30 ml. THF. After 2 hours at room temperature the mixture was diluted with $C_6H_6$ and $Et_2O$. The organic layer was washed in turn with $H_2O$, 2.5 N HCl, $NaHCO_3$ and brine, and taken to dryness.

The thus obtained crude N-octanoyl amide was dissolved in 70 ml. THF. This solution was cooled in ice and treated with 25 ml. N $B_2H_6$ in THF. Following 18 hours standing in the cold the mixture was worked up exactly as above. The crude amine was converted to the hydrochloride. This was recrystallized from EtOAc to give 2.95 g. (66%) of N-methyl-N-(n-octyl)-p-(1-adamantyloxy)aniline hydrochloride, m.p. 144°–148°.

Anal. Calcd for $C_{25}H_{40}ClNO$: C, 73.95; H, 9.39; N, 3.45. Found: C, 74.33; H, 9.62; N, 3.47.

EXAMPLE 60

3-Methyl-4-(1-adamantyloxy)-nitrobenzene

Sodium hydride (1.35 g. of 56% dispersion) was added to 4.90 g. of 1-adamantanol in 40 ml. DMF and 80 ml. $C_6H_6$. The mixture was heated at reflux for 1 hour and allowed to cool. There was then added 5.0 g. (0.032 mole) of (3-methyl-4-Fluoro)nitrobenzene. Following 17 hours heating at reflux, the mixture was allowed to cool, washed well with $H_2O$ and brine and taken to dryness. The dark residue was chromatographed on 1 L silica gel. (elution with 30% $CH_2Cl_2$ in SSB). The crystalline fractions were combined and recrystallized from a small amount of SSB. There was obtained 3.30 g. (36%) of 3-methyl-4-(1-adamantyloxy)nitrobenzene; m.p. 89.5°–91°.

Anal. Calcd for $C_{17}H_{21}NO_3$: C, 71.05; H, 7.37; N, 4.88. Found: C, 70.72; H, 7.46; N, 4.83.

EXAMPLE 61

4-(1-Adamamtyloxy)-nitronaphthalene

Sodium hydride (0.55 g. of a 56% dispersion) was added to 1.99 g. of 1-adamantanol in 20 ml. DMF and 40 ml. $C_6H_6$. The mixture was heated at reflux for 1 hour and allowed to cool. There was then added 2.50 g. (0.013 mole) of 4-fluoro nitronaphthalene. Following 17 hours heating at reflux the mixture was allowed to cool, washed well with $H_2O$ and brine and taken to dryness. The residue was chromatographed on 500 ml. silica gel (elution with 30% $CH_2Cl_2$ in SSB). The crystalline fractions were combined and recrystallized from $Me_2CO$:SSB. There was obtained 2.44 g. (58%) of 4-(1-adamantyloxy)-nitronaphthalene, m.p. 126°–128°.

Anal. Calcd for $C_{20}H_{21}NO_3$: C, 74.28; H, 6.55; N, 4.33. Found: C, 74.15; H, 6.59; N, 4.35.

EXAMPLE 62

3-Cyano-4-(1-adamantyloxy)nitrobenzene

Sodium hydride (1.68 g. of 58% dispersion) was added to 6.08 g. of 1-adamantanol in 40 ml. HMPA and 80 ml. $C_6H_6$. The mixture was heated at reflux for 1 hour and 7.28 g. (0.04 mole) of the (3-cyano-4-fluoro)nitrobenzene was added. Following 10 hours heating at reflux the mixture was allowed to cool, washed well with $H_2O$ and brine and taken to dryness. The dark residue was chromatographed on 1.2 L silica gel (elution with 3:1 $CH_2Cl_2$:SSB). Those fractions which were similar by TLC were combined and recrystallized from $Me_2CO$:SSB. There was obtained 0.83 g. (7%) of 3-cyano-4-(1-adamantyloxy)nitrobenzene, m.p. 187°–189°.

Anal. Calcd for $C_{17}H_{18}N_2O_3$: C, 68.44; H, 6.08; N, 9.39. Found: C, 68.28; H, 6.11; N, 9.24.

EXAMPLE 63

4-(1-Adamantyloxy)-m-toluidine Hydrochloride

A mixture of 3.30 g. (0.0115 mole) of 3-methyl-4-(1-adamantyloxy)-nitrobenzene and 0.35 g. 10% Pd/C in 150 ml. EtOAc was shaken under $H_2$ until the theoretical gas uptake was noted. The catalyst was removed by filtration and the filtrate taken to dryness. The residue was dissolved in $Et_2O$ and this treated with HCl in $Et_2O$. The precipitated solid was recrystallized from $CH_2Cl_2$:EtOAc. There was obtained 2.60 g. (77%) of 4-(1-adamantyloxy)-m-toluidine hydrochloride, m.p. 201°–202°.

Anal. Calcd for $C_{17}H_{24}ClNO$: C, 69.49; H, 8.23; N, 4.77. Found: C, 69.26; H, 8.06; N, 4.66.

EXAMPLE 64

4-(1-Adamantyloxy)-1-naphthalamine Hydrochloride

A mixture of 2.44 g. (0.0075 mole) of 4-(1-adamantyloxy)-nitronaphthalene and 0.25 g. 10% Pd/C in 150 ml. EtOAc was shaken under $H_2$ until the theoretical uptake of gas was observed (2 hours). The catalyst was removed by filtration and the filtrate taken to dryness. The residue was chromatographed on 200 ml. silica gel (elution with 20% $Me_2CO$:SSB). Those fractions which were similar by TLC were combined, dissolved in $Et_2O$ and treated with HCl in $Et_2O$. The resulting amorphous solid was dissolved in CH₂Cl₂ and precipitated by addition of SSB. There was obtained 1.63 g. of 4-(1-adamantyloxy)-1-naphthalamine hydrochloride as a non-crystalline solid.

Anal. Calcd for $C_{20}H_{24}ClNO$: C, 72.82; H, 7.33; N, 4.25. Found: C, 73.75; H, 7.82; N, 3.96.

EXAMPLE 65

4-Adamantoyloxy-N-methyl-N-(2-pyrrolidinoethyl)aniline Dihydrochloride Dihydrate To an ice:MeOH cooled solution of 2.0 g. (0.0078 mole) of N-Methyl-p-(1-adamantyloxy)aniline in 20 ml. THF was added 4.75 ml. of 1.64 N BuLi in pentane. A solution of a 1:1 mixture of toluene, and 1-chloro-2-pyrrolidino ethane (2.08 g.) in 20 ml. THF was then added and the mixture stirred at room temperature for 1 hour and at reflux for 18 hours. The solution was allowed to cool, diluted with C₆H₆ and washed with H₂O and brine. The residue remaining when the organic fraction was taken to dryness was dissolved in CH₂Cl₂, treated with 10 ml. HCl saturated Et₂O and taken to dryness. The residual solid was recrystallized from CH₂Cl₂:CH₃CN to yield 1.93 g. (55%) of 4-adamantyloxy-N-methyl-N-(2-pyrrolidinoethyl)aniline dihydrochloride dihydrate, m.p. 189°–190° (efervess).

Anal. Calcd for $C_{23}H_{36}Cl_2N_2O.2H_2O$: C, 59.59; H, 8.69; N, 6.04. Found: C, 59.82; H, 8.15; N, 5.82.

EXAMPLE 66

4-(1-Adamantyloxy)-N-methyl-N-[3-(dimethylamino)-propyl]aniline

To an ice:MeOH cooled solution of 2.0 g. (0.078 mole) of N-methyl-p-(1-adamantyloxy)aniline in 20 ml. THF was added 4.75 ml. of 1.64 N BuLi in pentane. A solution of a 1:1 mixture of toluene and 1-chloro-N,N-dimethyl propyl amine in 20 ml. THF was then added and the mixture stirred at room temperature for 1 hour and at reflux for 20 hours. The bulk of the solvent was removed in vacuum and the residue dissolved in H₂O and Et₂O. The organic layer was washed with H₂O and brine and taken to dryness. The residue was dissolved in CH₂Cl₂, treated with an excess of HCl in Et₂O and taken to dryness. The remaining solid was recrystallized from MeOH:CH₃CN to give 1.72 g. (53%) of 4'-(1-adamantyloxy)-N-methyl-N-[3-(dimethylamino)propyl]aniline, m.p. 221°–223°.

Anal. Calcd for $C_{22}H_{36}Cl_2N_2O.H_2O$: C, 60.96; H, 8.83; N, 6.46. Found: C, 61.19; H, 8.63; N, 6.14.

EXAMPLE 67

1-(1-Adamantyloxy)-4-iodobenzene

A solution of 5.0 g. (0.02 mole) of p-(1-adamantyloxy)aniline in 120 ml. of THF was added to a solution of 3.0 g. (0.026 mole) of isoamyl nitrite and 3.0 g. (0.012 mole) of I₂ in 65 ml. of C₆H₆. The mixture was stirred at room temperature for 1 hour, heated at reflux for 2 hours and then taken to dryness in vacuum. The residue was chromatographed on 1 L silica gel (elution with 20% CH₂Cl₂:SSB). The crystalline fractions were combined and recrystallized from SSB to give 2.77 g. (39%) of 1-(1-adamantyloxy)-4-iodobenzene, m.p. 118°–120°. The analytical sample melted at 115°–117.5°.

Anal. Calcd for $C_{16}H_{19}IO$: C, 54.25; H, 5.41. Found: C, 54.16; H, 5.53.

EXAMPLE 68

4-(1-Adamantyloxy)benzoic acid

BuLi (6.7 ml. of a 1.6 N pentane solution) was added to a dry ice:acetone cooled solution of 3.39 g. (0.096 mole) of 1-adamantyloxy-4-iodobenzene in 55 ml. of THF. The mixture was stirred in the cold for 2 hours, transferred onto dry ice under N₂, and allowed to stand at room temperature for 18 hours. The bulk of the solvent was evaporated in vacuum and the residue dissolved in H₂O and Et₂O. The organic fraction was extracted twice with N NaOH. All aqueous fractions were combined and acidified. A precipitated solid was collected on a filter and recrystallized from aqueous MeOH to yield 1.09 g. (42%) of 4-(1-adamantyloxy)-benzoic acid, m.p. 223°–225.5°. The analytical sample's melting point was 223°–226°.

Anal. Calcd for $C_{17}H_{20}O_3$: C, 74.97; H, 7.40. Found: C, 73.83; H, 7.39.

EXAMPLE 69

1-[p-(1-Adamantyloxy)benzoyl]-pyrrolidine

A solution of 2.45 g. (0.009 mole) of 4-adamantyloxybenzoic acid and 2.5 ml. of SOCl₂ in 55 ml. of C₆H₆ was heated at reflux for 4 hours and the solvent removed in vacuum. A solution of the residue (the acid chloride) in 23 ml. of THF was added to an ice cooled solution of 2.3 ml. of pyrrolidine in 55 ml. of THF and the mixture stirred at room temperature for 1 hour. The bulk of the solvent was removed in vacuum and the residue treated with H₂O. A precipitated gum solidified and was collected on a filter. Recrystallization from Et₂O:SSB yielded 2.19 g. (75%) of 1-[p-(1-adamantyloxy)benzoyl]pyrrolidine, m.p. 111°–113°. The analytical sample m.p. was 110.5°–112.5°.

Anal. Calcd for $C_{21}H_{27}NO_2$: C, 77.50; H, 8.36; N, 4.30. Found: C, 77.70; H, 8.30; N, 4.20.

EXAMPLE 70

4-(1-Adamantyloxy)-α-pyrrolidinotoluene

A solution of 1.69 g. (0.005 mole) of 1-[p-(1-adamantyloxy)benzoyl]-pyrrolidine in 90 ml. of THF was added to a well stirred suspension of 0.24 g. LiAlH₄ in 10 ml. of THF. Following 4 hours of melting at reflux the mixture was cooled in an ice bath. There was then added in turn 0.25 ml. H₂O, 0.25 ml. 15% NaOH and 0.75 ml H₂O. A precipitated gel was collected on a filter and the filtrate taken to dryness. The oily residue was dissolved in Et₂O and treated with an excess of HCl in Et₂O. The resulting solid was collected on a filter and recrystallized from MeOH:EtOAc to yield 1.11 g. (64%) of 4-(1-adamantyloxy)-α-pyrrolidinotoluene, m.p. 257°–258°.

Anal. Calcd for $C_{21}H_{30}ClNO$: C, 72.49; H, 8.69; N, 4.03. Found: C, 72.46; H, 8.89; N, 4.06.

EXAMPLE 71 p-[(2-Methyl-2-norbornyl)oxy)nitrobenzene

Methyl magnesium bromide (100 ml. of 3 M solution) was added to an ice cold solution of 22 g. (0.2 mole) of norcamphor in 200 ml. THF. Following 3 hours stirring in the cold the mixture was treated with 100 ml. saturated NH₄Cl. The organic layer was separated washed with H₂O and brine and taken to dryness to afford the alcohol: $\nu_{max}$ 3450 cm⁻¹. This was then used without further purification.

To a solution of 15.6 g. (0.10 mole) of the crude norborneol in 80 ml. DMF and 160 ml. $C_6H_6$ there was added 4.21 g. of 56% NaH dispersion. Following 30 minutes heating at reflux, there was added 14.1 g. of p-fluoronitrobenzene. The mixture was then heated for an additional 6 hours, cooled and washed thoroughly with $H_2O$ and brine. The residue was chromatographed on 2 L silica gel (elution with 1:1 SSB:$C_6H_6$). Those fractions which showed a single spot on tlc were combined to afford 13.5 g. of product as a yellow oil; the NMR is in agreement with the structure.

EXAMPLE 72 p-[(2-Methyl-2-norbornyl)oxy]aniline Hydrochloride

A mixture of 13.51 g. of p-[(2-methyl-2-norbornyl)oxy)-nitrobenzene and 0.65 g. 10% Pd/C in 150 ml. EtOAc was shaken under $H_2$ until the theoretical gas uptake was noted (20 minutes). The catalyst was removed by filtration and the filtrate taken to dryness. The residual oil was dissolved in $Et_2O$ and this treated with HCl in $Et_2O$. The precipitated solid was recrystallized from MeOH:EtOAc to give 10.63 g. of p-[(2-methyl-2-norbornyl)oxy]aniline hydrochloride, m.p. >290°; m/e 217.

Anal. Calcd for $C_{14}H_{20}ClNO$: C, 66.26; H, 7.94; N, 5.52. Found: C, 66.11; H, 7.96; N, 5.65.

EXAMPLE 73

1-[p-[(2-Methyl-2-norbornyl)oxy]phenyl]pyrrolidine and Hydrochloride

A mixture of the p-[(2-methyl-2-norbornyl)oxy]aniline prepared from 2.53 g. (0.01 mole) of the hydrochloride salt, 2.15 g. (1.18 ml.) of 1,4-dibromopentane and 2.80 g. $K_2CO_3$ in 25 ml. EtOH was heated at reflux overnight. The solvent was removed in vacuum and the residue dissolved in $H_2O$ and $Et_2O$. The organic layer was washed with $H_2O$ and brine and taken to dryness. A solution of the residue in $Et_2O$ was treated with a just sufficient amount of HCl in $Et_2O$. The precipitated solid was recrystallized from $CH_2CH$ to give 1.72 g. (56%) of 1-[p-[(2-methyl-2-norbornyl)oxy]phenyl]pyrrolidine and hydrochloride, m.p. 163°–164°; m/e 271.

Anal. Calcd for $C_{18}H_{26}ClNO$: C, 70.20; H, 8.51; 4.55. Found: C, 70.25; H, 8.76; N, 4.58.

EXAMPLE 74 p-(2-Methyl-2-norbornyl)oxy-aniline, Ethyl Carbamate

To an ice cold solution of p-[(2-methyl-2-norbornyl)oxy]aniline from 5.51 g. (0.022 mole) of the hydrochloride salt and 2.22 g. $Et_3N$ in 100 ml. THF, there was added dropwise 2.1 nl. $ClCO_2C_2H_5$. At the end of 17 hours in the cold, the solvent was removed in vacuum. The residue was dissolved in $H_2O$ and $Et_2O$. The organic layer was washed with $H_2O$ and brine and taken to dryness. The residue was recrystallized from $Me_2$. CO:SSB to give 4.84 g. (76%) of product, m.p. 91°–93°.

Anal. Calcd for $C_{17}H_{23}NO_3$: C, 70.56; H, 8.01; N, 4.84. Found: C, 70.96; H, 8.02; N, 4.43.

EXAMPLE 75

N-Methyl-p-(2-methyl-2-norbornyloxy)aniline Hydrochloride

A solution of 4.84 g. (0.017 mole) of p-(2-methyl-2-norbornyl)oxy)aniline, ethyl carbamate in 80 ml. THF was added to 1.0 g. $LiAlH_4$ in 20 ml. THF. At the end of 6.5 hours heating at reflux the mixture was cooled in ice and treated in turn with 1 ml. $H_2O$, 1 ml. 15% NaOH and 3 ml. $H_2O$. The inorganic gel was collected on a filter and the filtrate taken to dryness. The residue was dissolved in $Et_2O$ and treated with an equivalent of HCl in $Et_2O$. The precipitate was recrystallized from $CH_2Cl_2$:EtOAc. There was obtained 3.44 g. (76%) of N-methyl-p-(2-methyl-2-norbornyloxy)aniline hydrochloride, m.p. 161°–162°.

Anal. Calcd for $C_{15}H_{22}ClNO$: C, 67.27; H, 8.28; N, 5.23. Found: C, 67.07; H, 8.15; N, 4.88.

In Examples 10, 11, 27, 28, 35, 47, 50, 65, 69, 70 and 73 the 2,2'-dihalodiethylether of 2,2'-dihalodiethyl mercaptan that was used can be substituted to produce the corresponding morpholenes and thiomorpholenes.

EXAMPLE 76

2-Methyl-2-adamantanol

To 50 ml. of a 3.0 M etherial solution of $CH_3MgBr$ (0.15 mole of $CH_3MgBr$) in an additional 50 ml. of absolute ether cooled in an ice bath was added dropwise with stirring 15.0 g. (0.10 mole) of 2-adamantanone during forty-five minutes time. The mixture was then stirred for 18 hours at room temperature.

75 Ml of saturated aqueous $NH_4Cl$ was added, cautiously at first. Additional water and ether were added until all the solids dissolved. The ether layer was percolated through anhydrous $MgSO_4$ and concentrated to give 14.9 g. of white solid, m.p. 213.0–215.0.

Anal. Calcd for $C_{11}H_{18}O$: C, 79.46; H, 10.91; O, 9.62. Found: C, 79.19; H, 10.80.

EXAMPLE 77

4-(2-Methyl-2-adamantyloxy)-nitrobenzene

To 13.8 g. (0.0830 mole) of 2-methyl-2-adamantanol stirred in a mixture of 80 ml. of benzene and 40 ml. of DMF was added in portions 4.18 g. (0.087 mole of NaH) of 50% NaH in oil. Heating was commenced and when vigorous gas evolution was evident, the heat was lowered. When the reaction subsided, the mixture was refluxed for 20 minutes.

To this mixture, cooled almost to room temperature, was added 11.7 g. (0.0830 mole) of p-fluoronitrobenzene, and the mixture was refluxed for 6 hours. The mixture was allowed to cool.

Water and $CH_2Cl_2$ were added. The $CH_2Cl_2$ layer was washed with two 250 ml. portions of water, which were extracted with 100 ml. of $CH_2Cl_2$. The combined $CH_2Cl_2$ solutions were dried over anhydrous $MgSO_4$ and concentrated.

The crude product was chromatographed on 700 g. of silica gel, eluting with 1:1 Skellysolve B:$CH_2Cl_2$, to give 17.0 g. of product.

Anal. Calcd for $C_{17}H_{21}NO_3$: C, 71.06; H, 7.37; N, 4.87; O, 16.70; Found: C, 71.19; H, 7.48; N, 5.12.

EXAMPLE 78

4-(2-Methyl-2-adamantyloxy)aniline

A solution of 15.0 g. (0.0522 mole) of 4-(2-methyl-2-adamantyloxy)-nitrobenzene in 150 ml. of ethyl acetate was hydrogenated over 10% Pd/C. The crude product was recrystallized from $CH_2Cl_2$ and Skellysolve B to give 8.6 g. of light tan solid, m.p. 95.6°–97.9° C.

Anal. Calcd for $C_{17}H_{23}NO$: C, 79.33; H, 9.01; N, 5.44; O, 6.22. Found: C, 79.08; H, 8.95; N, 5.57.

By substituting for 2-methyl-2-adamantanol, trans-9-decalol, cis-9-decalol, 1,4a-(3'-methyl-1'-oxapropano)-trans-decahydronaphth-8a-ol, 1-diamantanol, 4-diamantanol, or 3-methyl-3-diamantanol, the correspondingly substituted compounds of the invention can be prepared following the procedure of the preceding examples 76–78.

EXAMPLE 79

4-(1-adamantyloxy)-3-chloronitrobenzene

To 73.8 g. (0.485 mole) of 1-adamantanol mixed intimately with 4.9 g. (0.049 mole) of cuprous chloride and warmed in an 80° oil bath was added 100 g. (0.485 mole) of dicyclohexylcarbodiimide. The mixture was heated for 18 hours and then 84.2 g. (0.485 mole) of 2-chloro-4-nitrophenol was added. The mixture was stirred and heated at 95°–110° for 24 hours.

The dark mixture was partially dissolved in about 1500 ml. of $CH_2Cl_2$, and the solution was filtered to give 78 g. of off-white solid which was discarded. The filtrate was washed with three 330 ml. portions of 10% NaOH and with brine (500 ml.). The $CH_2Cl_2$ solution was dried and concentrated to give a dark colored oil which was purified by chromatography on silica gel. The material thus obtained (11.0 g.) was recrystallized from acetone-Skellysolve B to afford 7.1 g. of white solid, m.p. 83.7–85.1. The IR and NMR spectra of the material were consistent with 4-(1-adamantyloxy)-3-chloronitrobenzene.

Anal. Calde for $C_{16}H_{18}ClNO_3$: C, 62.44; H, 5.89; N, 4.55; Cl, 11.52; O, 15.59. Found: C, 62.12; H, 6.01; N, 4.63; Cl, 11.62.

EXAMPLE 80

4-(1-adamantyloxy)-3-chloroaniline Hydrochloride 4.5 g. (0.0146 Mole) of 4-(1-adamantyloxy)-3-chloronitrogenzene was hydrogenated in ethyl acetate solution over platinum. The catalyst was removed by filtration through diatomaceous earth, and the solvent was removed in vacuo to give 4.2 g. of a red oil. This material was purified by chromatography on silica gel and then converted to the hydrochloride salt by treatment with HCl in $CH_2Cl_2$-ether solution. The hydrochloride was filtered, dried, and then purified by recrystallization from ethanol-ethyl acetate to give a gray solid, m.p. 178.8 (dec)-185.0 (dec). The IR spectrum of the material was consistent with the assigned structure.

Anal. Calcd for $C_{16}H_{21}Cl_2NO$: C, 61.15; H, 6.75; N, 4.46; Cl, 22.56; O, 5.09. Found: C, 61.23; H, 6.77; N, 4.16; Cl, 22.44.

EXAMPLE 81

N-[4-(1Adamantyloxy)-3-chlorophenyl]-pyrrolidine 1.7 g. (0.00612 Mole) of 4-(1-adamantyloxy)-3-chloroaniline, 1.32 g. (0.00612 mole) of 1,4-dibromobutane and 1.86 g. (0.0135 mole) of potassium carbonate were combined in 50 ml. of absolute ethanol and refluxed for 18 hours.

The mixture was cooled and evaporated to dryness. The residue was dissolved in 150 ml. of $CH_2Cl_2$ and washed with two 200 ml. portions of water; the combined aqueous layers were extracted with 50 ml. of $CH_2Cl_2$. The combined $CH_2Cl_2$ layers were dried (anhydrous $MgSO_4$) and concentrated to give 2.1 g. of a red oil which was purified by recrystallization (absolute ethanol) and chromatography on silica gel. The resulting white solid, m.p. 157.2–158.3, gave NMR and IR spectra consistent with the assigned structure.

Anal. Calcd for $C_{20}H_{26}ClNO$: C, 72.38; H, 7.90; N, 4.22; Cl, 10.68; O, 4.82. Found: C, 71.72; H, 8.03; N, 4.35; Cl, 11.41.

EXAMPLE 82

4-(1-Adamantyloxy)-3,5-dimethylnitrobenzene

In accordance with the foregoing procedure, the above compound was prepared, m.p. 142.9–153.2. NMR and IR spectra were in accord with the assigned structure.

Anal. Calcd for $C_{18}H_{23}NO_3$: C, 71.73; H, 7.69; N, 4.65; O, 15.93.

EXAMPLE 83

4-(1-Adamantyloxy)-3,5-dimethylaniline hydrochloride

In accordance with the foregoing procedure, the above compound was prepared, m.p. 196.7–197.0. NMR and IR spectra were consistent with the assigned structure.

Anal. Calcd for $C_{18}H_{26}ClNO$: C, 70.23; H, 8.51; N, 4.55; Cl, 11.52; O, 5.20. Found: C, 70.02; H, 8.17; N, 4.20; Cl, 11.42.

By substituting 2-nitro-4-pyrrolidyl phenol or 2-pyrrolidyl-4-nitrophenyl in the foregoing examples 79 to 81 the corresponding di-pyrrolidyl compounds can be prepared.

EXAMPLE 84

N-[4-(1-Adamantyloxy)-3,5-dimethylphenyl]pyrrolidine

In accordance with the foregoing procedure, the above compound was prepared, m.p. 93.0–102.5, gave reasonable NMR and IR spectra.

Anal. Calcd for $C_{22}H_{31}NO$: C, 81.18; H, 9.60; N, 4.30; O, 4.92. Found: C, 81.27; H, 9.98; N, 4.34.

EXAMPLE 85

4-(1-Adamantyloxy)-3,5-dimethylnitrobenzene

To 73.8 g. (0.485 mole) of 1-adamantanol intimately mixed with 4.9 g. (0.049 mole) of CuCl in a 1 liter 3-neck flask warmed in an 85° oil bath was added 100 g. (0.485 mole) of dicyclohexylcarbodiimide, and the mixture was stirred mechanically and heated in a 90°–100° oil bath for approproximately 21 hours.

81.1 g. (0.485 mole) of 4-nitro-2,6-dimethyl phenol was added, and the mixture was stirred at 100°–110° for approximately 20 hours.

The mixture was cooled and rinsed out of the flask with $CH_2Cl_2$. The combined $CH_2Cl_2$ rinses were filtered to remove a solid which was discarded. The filtrate was washed with three 300 ml. portions of 10% NaOH and brine, and it was dried (anhydrous $MgSO_4$) and concentrated to give 86 g. of a black semi-solid. The crude material was chromatographed on silica gel, affording the desired product, a white solid, m.p. 142.9–153.2. NMR and IR spectra were in accord with the assigned structure.

Anal. Calcd for $C_{18}H_{23}NO_3$: C, 71.73; H, 7.69; N, 4.65; O, 15.93. Found: C, 70.76; H, 7.62; N, 4.44.

EXAMPLE 86

4-(1-Adamantyloxy)-3,5-dimethylaniline hydrochloride 11.5 g. Of a mixture of 4-(1-adamantyloxy)-3,5-dimethyl nitrobenzene and bis(1-adamantyl)ether was hydrogenated over 10% Pd on carbon in ethyl acetate solution. The catalyst was filtered and the filtrate was treated with 16.4 ml. of 3.5 N HCl in ether, producing a flocculent precipitate, which was filtered and dried in vacuo to give 6.4 g. of white solid hydrochloride, m.p. 196.7–197.0. NMR and IR spectra were consistent with the assigned structure.

Anal. Calcd for $C_{18}H_{26}ClNO$: C, 70.23; H, 8.51; N, 4.55; Cl, 11.52; O, 5.20. Found: C, 70.02; H, 8.17; N, 4.20; Cl, 11.42.

EXAMPLE 87

N-[4-(1-Adamantyloxy)-3,5-dimethylphenyl]pyrrolidine

The amine obtained by washing a $CH_2Cl_2$ solution of 2.1 g. (6.82 mmole) of 4-(1-adamantyloxy)-3,5-dimethylaniline hydrochloride with three 25 ml. portions of 10% aq. NaOH followed by a water wash, drying (anhydrous $MgSO_4$) and concentration, was combined with 1.47 g. (6.82 mmole) of 1,4-dibromobutane and 2.07 g. (15.0 mmole) of $K_2CO_3$ in 20 ml. of absolute ethanol and refluxed for approximately 18 hours.

The mixture was cooled and evaporated to dryness, and the residue was dissolved in 150 ml. of $CH_2Cl_2$ and washed with two 200 ml. portions of water. The combined aqueous layers were extracted with 50 ml. of $CH_2Cl_2$ and the combined $CH_2Cl_2$ layers were dried (anhydrous $MgSO_4$) and concentrated to give 2.1 g. of a red oil which solidified and was recrystallized from ethanol. The mother liquor contained starting material and so it was evaporated to dryness and mixed with 0.66 g. of 1,4-dibromobutane and 0.93 g. of $K_2CO_3$ in 20 ml. of absolute ethanol and refluxed for approximately 18 hours. The mixture was worked up as just described and this crude product, combined with the recrystallized solid from above, was purified by silica gel chromatography to give a tan solid which was repeatedly dried in vacuo, affording a brown solid m.p. 93.0°–102.5° C. NMR and IR spectra were consistent with the assigned structure.

Anal. Calcd for $C_{22}H_{13}NO$: C, 81.18, H, 9.60; N, 4.30. Found: C, 81.27; H, 9.98; N, 4.34.

EXAMPLE 88

4-(1-Adamantyloxy)-2-(methylthiomethyl)-aniline

To 6.2 g. (0.088 mole) of chlorine in 240 ml. of $CH_2Cl_2$ in a one-liter 3-neck flask cooled to $-70°$ to $-73°$ was added dropwise with stirring a cold ($\sim -70°$) solution of 5.7 g. (0.092 mole) of dimethyl sulfide in 20 ml. of $CH_2Cl_2$. The solution was stirred for several minutes, and then a solution of 21.4 g. (0.088 mole) of 4-(1-adamantyloxy)-aniline and 8.9 g. (0.088 mole) of triethylamine in 400 ml. of $CH_2Cl_2$ cooled either to $-70°$ or to $-40°$ to $-50°$ was added dropwise rapidly. Then the mixture was either stirred at $-70°$ and gradually allowed to warm to room temperature during four hours and then cooled again to $-65°$ or it was stirred at $-70°$ for two hours followed in either case by the addition of 51.8 g. of 25% sodium methoxide in methanol solution, removal of the cold bath, and stirring at room temperature for 12 to 18 hours.

The reaction mixture was washed with three 1 liter portions of water, dried (anhydrous $MgSO_4$), and concentrated to give a red oily product which was purified by chromatography on silica gel to give a yellowish solid product, which could be recrystallized from $CH_2Cl_2$-Skellysolve B to afford a light yellow solid, m.p. 62.0–65.0. The NMR spectrum was in accord with the structure assigned.

Anal. Calcd for $C_{18}H_{25}NOS$: C, 71.24; H, 8.30; N, 4.62; S, 10.57. Found: C, 71.52; H, 8.58; N, 4.64; S, 10.38.

EXAMPLE 89

4-(1-adamantyloxy)-2-methylaniline 23.2 g. (0.0764 mole) of 4-(1-adamantyloxy)-2-(methylthiomethyl)-aniline was stirred for 2 hours with approximately 96 g. of Raney nickel in 600 ml. of absolute ethanol. The catalyst was filtered and the solvent was evaporated. Purification by chromatography on silica gel followed by recrystallization from $CH_2Cl_2$-Skellysolve B afforded the desired product, a tan solid, m.p. 143.4°–145.1° C. The NMR spectrum was in accord with the assigned structure.

Anal. Calcd for $C_{18}H_{23}NO$: C, 79.33; H, 9.01; N, 5.44. Found: C, 78.64; H, 8.93; N, 5.54.

EXAMPLE 90

4-(1-adamantyloxy)-2-fluoronitrobenzene

To 45.7 g. (0.300 mole) of 1-adamantanol intimitely mixed with 2.97 g. (0.030 mole) of CuCl in a one-liter 3-neck flask warmed in an 85° oil bath was added 70.2 g. (0.34 mole) of dicyclohexyl carbodiimide, and the mixture was stirred mechanically and heated in an 80° oil bath for approximately 20 hours.

47.1 g. of 3-fluoro-4-nitrophenol was added all at once, and the mixture was stirred at 80°–100° for 20 hours.

The mixture was cooled, digested with 600 ml. of $CH_2Cl_2$, and filtered off a white solid which was discarded. The filtrate was washed with three 200 ml. portions of 10% aq. NaOH and 1 liter of water; the $CH_2Cl_2$ layer was dried (anhydrous $MgSO_4$) and concentrated.

The crude product was purified by silica gel chromatography to give the desired product, a light yellow solid, m.p. 88.0–89.0. The NMR spectrum of this material was consistent with the assigned structure.

Anal. Calc'd for $C_{16}H_{18}FNO_3$: C, 65.97; H, 6.23; N, 4.81; F, 6.52; O, 16.48. Found: C, 66.15; H, 6.32; N, 4.55; F, 6.26.

EXAMPLE 91

4-(1-Adamantyloxy)-2-fluoroaniline a. 4-(1-Adamantyloxy-2-fluoronitrobenzene

To 45.7 g (0.300 mole) of 1-adamantanol intimitely mixed with 2.97 g (0.030 mole) of CuCl in a one-liter 3-necked flask warmed in an 85° oil bath is added 70.2 g (0.34 mole) of dicyclohexylcarbodiimide, and the mixture is stirred mechanically and heated in an 80° oil bath for approximately twenty hours.

47.1 g of 3-fluoro-4-nitrophenol is added all at once, and the mixture stirred at 80°–100° for twenty hours.

The mixture is cooled, digested with 600 ml of $CH_2Cl_2$, and filtered. A white solid is discarded. The filtrate is washed with three 200 ml portions of 10% aqueous NaOH and 1 liter of water. The $CH_2Cl_2$ layer is dried and concentrated.

The crude product is chromatographed on 4000 g of silica gel, collecting 300 ml fractions (except for two initial fractions totaling 6 liters). Fraction 5 contained 3.0 g of light yellow solid product, m.p. 88.0–89.0. The nmr and ir spectra were consistent with the structure.

Anal. Calcd. for $C_{16}H_{18}FNO$: C, 65.97; H, 6.23; N, 4.81; F, 6.52. Found: C, 66.15; H, 6.32; N, 4.55; F, 6.26.

b. 13.4 g of 4-(1-adamantyloxy)-2-fluoronitrobenzene (approximately 80% pure; 0.037 mole) in ethyl acetate solution was hydrogenated for two hours over platinum (from 1.0 g of $PtO_2$). The catalyst was filtered and the solvent was evaporated to give 13.1 g of white solid, which was purified by two recrystallizations from $CH_2Cl_2$-Skellysolve B, affording a pink solid, m.p. 152.0–154.0. The NMR spectrum of this material was consistent with the assigned structure.

Anal. Calcd. for $C_{16}H_{20}FNO$: C, 73.54; H, 7.71; F, 7.27; N, 5.36; O, 6.12. Found: C, 73.32; H, 7.89; F, 7.18; N, 5.22.

EXAMPLE 92

N-[4-(1-Adamantyloxy)phenyl]morpholine

To 12.2 g (0.050 mole) of 4-(1-adamantyloxy)aniline dissolved in 200 ml of THF cooled in an ice bath was added dropwise with stirring 47 ml of a 1.07 M solution of n-BuLi in hexane. During the addition 100 ml of THF was added to the reaction mixture, and the mixture was stirred for one hour. 7.16 g (0.050 mole) of bis(2-chloroethyl)ether was added (as a solution in THF) and the mixture was refluxed for nineteen hours and allowed to cool. An additional 47 ml of the 1.07 M solution of n-BuLi in hexane was added dropwise with stirring to the reaction mixture cooled in an ice bath, and the mixture was stirred for one hour at room temperature and refluxed for twenty-three hours.

The THF was evaporated, and water and $CH_2Cl_2$ were added. The $CH_2Cl_2$ layer was washed with water, dried (anhydrous $MgSO_4$), and evaporated to give a light brown solid which was recrystallized from $CH_2Cl_2$-Skellysolve B, affording the desired product, which was dried repeatedly in vacuo at 50°–100°, and 60° to give a brown solid, m.p. 146.9–149.7.

The NMR and IR spectra were in accord with the assigned structure.

Anal. Calcd. for $C_{20}H_{27}NO_2$: C, 76.64; H, 8.68; N, 4.47; O, 10.21. Found: C, 74.43; H, 8.67; N, 4.48.

EXAMPLE 93

N-Methyl-4'-(1-adamantyloxy)acetanilide

To 11.4 g (44.3 mmoles) of N-methyl-4'-(1-adamantyloxy)aniline in part of 120 ml of THF is added in one portion 6.22 g (60.9 mmoles) of acetic anhydride in the balance of the THF. The solution warms slightly and is stirred overnight. The mixture is evaporated to dryness to give a yellow solid. Three crystallizations from boiling methanol gives 3.6 g of light maroon solid, m.p. 168.3–170.3.

Anal. Calcd. for $C_{19}H_{25}NO_2$: C, 76.22; H, 8.42; N, 4.68. Found: C, 75.85; H, 8.28; N, 4.51.

EXAMPLE 94

4'-(1-Adamantyloxy)-2'-fluoroacetanilide 1.6 g (6.12 mmoles) of 4-(1-Adamantoyloxy)-2-fluoroaniline and 0.86 g (8.43 mmoles) of acetic anhydride are mixed in 25 ml of THF and stirred at 25° for three days. The solvent is evaporated to give 1.8 g of pink solid which is recrystallized from methanol (15 ml) to give 1.3 g of white solid, m.p. 173.2–175.0.

The NMR and IR spectra are in accord with the structure.

Anal. Calcd. for $C_{18}H_{22}FNO_2$: C, 71.26; H, 7.31; N, 4.62; F, 6.26. Found: C, 71.64; H, 7.38; N, 4.62; F, 5.94.

EXAMPLE 95

1-[4-(Adamantyloxy)-2-fluorophenyl]pyrrolidine

A mixture of 2.3 g (8.8 mmoles) of 4-(1-adamantyloxy)-2-fluoroaniline, 1.90 g (8.80 mmoles) of 1,4-dibromobutane, and 2.68 g (19.4 mmoles) of $K_2CO_3$ in deaerated absolute ethanol (25 ml) is refluxed for twenty-four hours. The solvent is evaporated, and the residue taken up in methylene chloride (125 ml) and water (125 ml). The methylene chloride layer is washed with 2×125 ml of water, and the combined aqueous portions are extracted with methylene chloride (50 ml). The combined methylene chloride layers are dried and concentrated. The crude product is chromatographed by high pressure liquid chromatography on a 2.54×109 cm column at approximately 40 psi, eluting with 0.5% acetone in methylene chloride and collecting 200 ml fractions. Fraction 3 contains 1.5 g of tan solid, m.p. 99.0°–105.9° C.

The NMR and IR spectra are consistent with the structure.

Anal. Calcd. for $C_{20}H_{26}FNO$: C, 76.16; H, 8.31; N, 4.44; F, 6.02. Found: C, 76.09; H, 8.26; N, 4.12; F, 5.90.

EXAMPLE 96

4-(Adamantyloxy)-2-methyl-6-[(methylthio)methyl]aniline hydrochloride 5.70 g (80.4 mmoles) of chlorine, 5.22 g (84.1 mmoles) of dimethyl sulfide, 20.7 g (80.4 mmoles) of 4-(adamantyloxy)-2-(methylaniline), 8.14 g (80.4 mmoles) of triethylamine and 23.7 g of 25% $NaOCH_3$ in $CH_3OH$ (5.92 g $NaOCH_3$, 110 mmoles) are reacted in a manner similar to Example 88. There results 27.4 g of red-brown oil which is chromatographed on 4500 g of silica gel eluting with 1% acetone in $CH_2Cl_2$ (6 l), 2% acetone in $CH_2Cl_2$ (12 l), 3% acetone in $CH_2CL_2$ (15 l), and 4% acetone in $CH_2Cl_2$ (6 l). Except for 4 initial fractions totaling 14 l, 300 ml fractions are collected. Fractions 15–30 contain the desired product (12.4 g, 54.1% yield) in acceptable purity. Fractions 18 and 20 (3.5 g) were chromatographed on 750 g of silica gel with the same solvent system to afford 2.8 g of red oil. Conversion of this oil to the hydrochloride in $CH_2Cl_2$-ether gives a solid containing 7% $CH_2Cl_2$ which could not be removed. The regenerated free base is dried in vacuo for seventy-two hours at 55°, and then treated with hydrochloric acid in ether. The hydrochloride of the desired product is filtered, washed with ether and dried to give 2.2 g of off-white solid, m.p. 202.2–203.3

Anal. Calcd. for $C_{19}H_{27}NOS.HCl$: C, 64.47; H, 7.97; Cl, 10.02; N, 3.96; S, 9.06. Found: S, 64.80; H, 7.92; Cl, 9.67; N, 3.76; S, 9.10.

EXAMPLE 97

4-(1-Adamantyloxy)-2,6-dimethylaniline 9.6 g (33.6 mmoles) of 4-(1-adamantyloxy)-2-(methylthiomethyl)-6-methylaniline is disulfurized as in Example 89 using six rounded teaspoonfuls of Raney nickel sludge (approximately 48 g of Raney nickel). The product is chromatographed by HPLC on a 5.1 cm×109 cm column at 30 psi, eluting with $CH_2Cl_2$ followed by 0.5% acetone in $CH_2Cl_2$, 5 l., 0.75% acetone in $CH_2Cl_2$, 3 l., and 1% acetone in $CH_2Cl_2$, 5 l., affording 2.7 g of red solid. Center fractions (0.9 g) give product of m.p. 132.6–139.0.

Anal. Calcd. for $C_{18}H_{25}NO$ (accounting for 1.47% $CH_2Cl_2$ content): C, 78.70; H, 9.18; N, 5.08. Found: C, 78.97; H, 9.25; N, 4.93.

EXAMPLE 98

[4-(1-Adamantyloxy)-2,6-dimethylphenyl]pyrrolidine

A mixture of 1.8 g (6.63 mmoles) of 4-(1-adamantyloxy)-2,6-dimethylaniline, 1.43 g (6.63 mmoles) of 1,4-dibromobutane, and 2.01 g (14.6 mmoles) of $K_2CO_3$ in 25 ml deaerated absolute ethanol is refluxed for forty-five hours, cooled, and evaporated. The residue is taken up in $CH_2Cl_2$ (125 ml) and water (125 ml). The $CH_2Cl_2$ layer is washed with water, and the combined aqueous layers are extracted with $CH_2Cl_2$ (50 ml.). The combined organic layers are dried and concentrated to give 2.4 g of a brown oil, which is chromatographed by HPLC on a 2.54 cm × 109 cm column at 40 psi eluting with 0.5% acetone in $CH_2Cl_2$ and then 0.75% acetone in $CH_2Cl_2$ to give 0.45 g in the first liter eluted from the column. This solid in 1 ml of $CH_2Cl_2$ and 5 ml of ether is treated with 3.5 N HCl in ether. The hydrochloride is filtered, washed with ether, and dried to give 0.38 g of white solid, m.p. 184.4–185.6 (dec.).

Anal. Calcd. for $C_{22}H_{31}NO \cdot HCl$ (accounting for 1.08% diethyl ether and 1.85% $CH_2Cl_2$): C, 71.82; H, 8.84; N, 3.76; Cl, 11.04. Found: C, 72.09; H, 8.98; N, 3.92; Cl, 10.54.

EXAMPLE 99 p-(1-Diamantyloxy)aniline a. 1-Bromodiamantane

To 3.1 g (16.5 mmole) of diamantane is added 10 ml of bromine. Vigorous evolution of gas is evident, but the mixture warms only slightly. The mixture is stirred for one hour and then the excess bromine is evaporated. The crude solid is dissolved in 75 ml of $CH_2Cl_2$ and washed twice with 10% $NaHSO_3$ and once with water. The $CH_2Cl_2$ solution is dried ($MgSO_4$) and concentrated to give 5.4 g of light brown solid. 1.0 g of this material is sublimed (0.20 mm Hg and 105° oil bath) to give 0.84 g of white solid 1-bromodiamantane.

Anal. Calcd. for $C_{14}H_{19}Br$: C, 62.93; H, 7.17; Br, 29.90. Found: C, 63.25; H, 7.43; Br, 29.49.

b. 1-Diamantanol

To a solution of 4.4 g (16.5 mmoles) of 1-bromodiamantane in 60 ml of dioxane is added a solution of 7.59 g of silver nitrate in 20 ml of water, immediately producing a white granular precipitate. Gas chromatographic analysis of an aliquot shows that no starting bromide remains. During the gas chromatographic analysis the mixture is brought to reflux, which is, however, discontinued after only 0.5 hour. The hot mixture is filtered and allowed to cool. The white needles are filtered and dried in vacuo at 50° to give 1.7 g of off-white solid, which is sublimed (0.3 mm, 100°–130° oil bath) to give 1.6 g (56% yield) of white solid 1-diamantanol, m.p. 285.2°–291.0° C.

Anal. Calcd. for $C_{14}H_{20}O$: C, 82.30; H, 9.87. Found: C, 82.26; H, 10.02.

c. 4-(1-Diamantyloxy)nitrobenzene

To 22.2 g (0.109 mole) of 1-diamantanol almost completely dissolved in 225 ml of benzene and 113 ml of dimethylformamide is added 5.05 g (0.120 mole) of sodium hydride in oil. The mixture is heated, and when vigorous gas evolution begins, the heat source is removed. After a few minutes the reaction subsides, and the mixture is refluxed for twenty minutes. After the mixture cools, 15.4 g (0.109 mole) of p-fluoronitrobenzene in 10 ml of benzene is added dropwise. No exotherm is observed, and the mixture is refluxed for six hours. Both water and $CH_2Cl_2$ are added to the cooled reaction mixture. The organic layer is washed with three additional 500 ml portions of water which are kept separate. The four aqueous portions are extracted in succession with the same 200 ml portion of $CH_2Cl_2$. The combined organic portions are dried and concentrated to give 47 g of yellow solid, which is triturated with two 50 ml portions of ether, affording 20.3 g of light yellow solid product. A second crop of 2.6 g was obtained from the mother liquor; (total yield: 22.9 g; 65%). Recrystallization of the second crop from hexane and then ethanol affords the analytical sample, m.p. 140.5–142.0. The nmr and ir spectra are in accord with the structure.

Anal. Calcd. for $C_{20}H_{23}NO_3$: C, 73.82; H, 7.12; N, 4.30. Found: C, 73.65; H, 7.17, N, 4.15.

d. 4-(1-Diamantyloxy)aniline 20.3 g (62.4 mmole) of 4-(1-diamantyloxy)nitrobenzene in 1100 ml of ethyl acetate is hydrogenated over 10% palladium over carbon. The catalyst is filtered through Solka-floc filter aid, and the solvent evaporated to give 18.5 g of white solid, which is dissolved in 60 ml of $CH_2Cl_2$, diluted with 60 ml of hexane, and allowed to crystallize. 13.6 g (73.9% yield) of pink solid product, m.p. 128.8–135.8, results.

Recrystallization from ethanol gives the analytical sample.

Anal. Calcd. for $C_{20}H_{25}NO$: C, 81.31; H, 8.53; N, 4.74. Found: C, 81.56; H, 8.43; N, 4.37.

EXAMPLE 100

1-[4-(1-Diamantyloxy)phenyl]pyrrolidine

A mixture of 4.43 g (15.0 mmoles) of 4-(1-diamantyloxy)aniline, 3.24 g (15.0 mmoles) of 1,4-dibromobutane, and 4.56 g (33.0 mmoles) of potassium carbonate in 30 ml. of deaerated absolute ethanol is maintained at reflux for twenty-four hours. The solvent is evaporated, and the residue worked up to give 5.2 g of white solid product which is chromatographed on a 1×43 inch HPLC column, eluting with 0.5% acetone in $CH_2Cl_2$. A total of 3.3 g (63.0%) of off-white solid is obtained from the second and third 200 ml fractions.

The analytical sample is obtained by a second chromatography followed by recrystallization from absolute ethanol.

Anal. Calcd. for $C_{24}H_{31}NO$: C, 82.48; H, 8.94; N, 4.01. Found: C, 82.06; H, 9.19; N, 3.65.

EXAMPLE 101

4'-(1-Diamantyloxy)acetanilide

To 4.5 g (15.2 mmoles) of 4-(1-diamantyloxy)aniline in 50 ml of tetrahydrofuran cooled in an ice bath is added 2.14 g (20.9 mmoles) of acetic anhydride, and the mixture is swirled and allowed to stand at room temperature. A white solid gradually precipitates and no starting material remains after six hours. The solvent is evaporated and the pink solid is recrystallized from 300 ml of methanol to give 3.8 g (74.1%) of tan solid product, m.p. 186.1°–189.7° C.

Anal. Calcd. for $C_{22}H_{27}NO_2$: C, 78.30; H, 8.06; N, 4.15. Found: C, 78.16, H, 8.20; N, 4.13.

EXAMPLE 102

N-[4-(1-Adamantyloxy)phenyl]pyrrolidine-Hydrochloride

To 29.8 g (0.100 mole) of N-[4-(1-adamantyloxy)phenyl]pyrrolidine dissolved in $CH_2Cl_2$ (200 ml) and diethyl ether (25 ml) stirred and cooled in an ice bath is added in one portion 44 ml of 3.4 N HCl in ether (0.15 mole of HCl). After thirty minutes' stirring, the solvent is evaporated. The resulting solid (33.8 g) is recrystallized from $CH_2Cl_2$ (120 ml)-diethyl ether (100 ml) to give 29.0 g of white solid product, mp (in bath at 148°; 1°/minute temperature rise), 163.4°–166.8° C. Nmr, ir, and UV spectra were in accord with the structure.

Anal. Calcd. for $C_{20}H_{28}ClNO$: C, 71.94; H, 8.45; N, 4.19; Cl, 10.62. Found: C, 72.28; H, 8.71; N, 4.35; Cl, 10.66.

EXAMPLE 103

4-(1-Adamantyloxy)-3-fluoroaniline a. 3,4-Difluoronitrobenzene

This material is prepared as described by R. W. Taft, G. B. Klingensmith, and S. Ehrenson (*J. Am. Chem. Soc.*, 87, 3620 (1965)). To a stirred mixture of 5.0 ml of concentrated nitric acid and 13.9 ml of concentrated sulfuric acid cooled to −12° C. is added 9.7 g (0.085 mole) of 1,2-difluorobenzene. A slight exotherm is observed and the mixture is cooled to −20° C. whereupon it solidifies. The mixture is stirred for forty-five minutes at −5° to 0° and is then allowed to warm slowly to room temperature. After one hour the mixture is poured onto ice, and the mixture extracted with diethyl ether (3×75 ml). The combined ether extracts are washed with water, 10% aqueous $Na_2CO_3$, and water again. The ether solution is dried ($MgSO_4$) and concentrated in vacuo without external heating to give the crude product (11.9 g), which is distilled (kugelrohr apparatus) to give 10.2 g of colorless liquid. The nmr spectrum of this material is consistent with the structure.

b. 4-(1-Adamantyloxy)-3-fluoronitrobenzene

A mixture of 16 g (64 mmoles) of 1-adamantanol, 3.35 g (70 mmoles NaH) of 50% NaH in oil, 60 ml of benzene, and 60 ml of dimethylformamide is heated until hydrogen is vigorously evolved (80°). Heating is discontinued until the effervescence subsides, and then the mixture is heated at 90° for 0.5 hour. To this mixture cooled to 20° is added dropwise with stirring 9.7 g (63 mmoles) of 3,4-difluoronitrobenzene. A slight exotherm is observed, and the mixture is refluxed (110°) for sixty-four hours. Water (300 ml) is added to the cooled mixture, and it is extracted with $CH_2Cl_2$ (200 ml). The $CH_2Cl_2$ layer is washed with water (3×300 ml), and the four separate wash water portions are extracted in succession with the same 200 ml of $CH_2Cl_2$. The combined organic layers are dried, and concentrated to give 31.5 g of solid crude product, which is chromatographed on silica gel (3100 g), eluting with $CH_2Cl_2$, and taking 500 ml fractions. Fractions 14 and 15 contain 12.6 g of white solid product, m.p. 110.1–118.2, as confirmed by nmr spectroscopy.

Anal. Calcd. for $C_{16}H_{18}FNO$: C, 65.97; H, 6.23; N, 4.81. Found: C, 65.95; H, 6.30; N, 4.76.

c. 4-(1-Adamantyloxy)-3-fluoroaniline

A solution of 11.4 g (39.1 mmoles) of 4-(1-adamantyloxy)-3-fluoronitrobenzene in ethyl acetate (500 ml) is hydrogenated over platinum. The catalyst is filtered through a cake of Solka-floc filter aid, and the solvent is evaporated to give 10.6 g of white solid, which is recrystallized from $CH_2Cl_2$ (75 ml)-hexane (75 ml). There results 7.7 g of white solid, m.p. 179.2–189.0. The nmr spectrum of this material confirms that it is 4-(1-adamantyloxy)-3-fluoroaniline.

EXAMPLE 104

4'-(1-Adamantyloxy)-3'-fluoroacetanilide

To 2.61 g (10.0 mmoles) of 4-(1-adamantyloxy)-3-fluoroaniline dissolved in 40 ml of tetrahydrofuran is added 1.41 g (13.8 mmoles) of acetic anhydride. The mixture is allowed to stand for two days and then the solvent is evaporated to give a white solid. This crude product is dissolved in 220 ml of boiling methanol, and the solution filtered and concentrated to 25 ml. Suction filtration and drying affords 2.6 g of fluffy white solid, m.p. 228.0–230.4. The structure of the product is confirmed as 4'-(1-adamantyloxy)-3'-fluoroacetanilide by its nmr spectrum.

EXAMPLE 105

N-[4-(1-Adamantyloxy)-3-fluorophenyl]pyrrolidine

A mixture of 4.9 g (19 mmoles) of 4-(1-adamantyloxy)-3-fluoroaniline, 4.1 g (19 mmoles) of 1,4-dibromobutane, and 5.7 g (41.4 mmoles) of potassium carbonate in 350 ml of deaerated absolute ethanol is refluxed for three days and allowed to cool, and the solvent is evaporated. Water (∼300 ml) is added to the residue and the mixture is extracted with $CH_2Cl_2$ (250 ml). The organic layer is washed again with water and the combined aqueous portions extracted with $CH_2Cl_2$ (100 ml). The combined $CH_2Cl_2$ portions are dried ($MgSO_4$) and concentrated to give 5.7 g of crude off-white solid. This material is chromatographed by HPLC on a 2.5×109 cm column, eluting with 0.5% acetone in $CH_2Cl_2$, and taking 210 ml fractions. The second fraction contains 1.1 g of somewhat impure product. Sublimation of a portion of this material (0.1 mm, 115°–135° oil bath) affords purer white solid, m.p. 150–153.4, the nmr spectrum of which confirms the structure as N-[4-(1-adamantyloxy)-3-fluorophenyl]pyrrolidine.

In the foregoing examples the reactions applied in the synthesis of the various derivatives of adamantane are applicable in the same manner, considering, for example, the aniline derivatives, to the preparation of other analogous bridged polycyclic, particularly bicyclooctane and 2-methyl-2-norborane derivatives.

Representative compounds of the invention were tested in hypercholesterolemic weanling rats. The compounds were administered orally for four days to weanling male rats fed a 1.5% cholesterol 0.5% cholic acid containing diet for seven days. The rats were weanling albino rats housed in groups of five animals which were allowed free access to food and water for three days before being distributed by weight into experimental groups. The diet of Phillips and Berg (J. Nutr. 53. 481–498, 1945) was used, with 10% coconut oil substituted for corn oil and 18% casein and 0.2% methionine as a protein source and with 1½% cholesterol and 0.5% cholic acid added to the diet at the expense of dextrine. This diet was continued for seven days. The last four days test compounds suspended in 0.25% aqueous methylcellulose were administered by stomach tube. After an overnight fast they were anesthetized with Cyclopal, bled and the serum analyzed for cholesterol and heparin precipitating lipoproteins (HPL). The results are given as treated/control ratios of the antilogs of log means derived from six treated and twenty-four control animals. Statistical difference from control means ($p \leq 0.05$) were determined by Student's test using pooled error variance (Steele et al. in "Principles and Procedures of Statistics", McGraw-Hill, New York, 1960, p. 106). The acceptance of an assay required an appropriate response to 50 mg/kg of a positive standard p-(1-adamantyloxy)aniline and a negative standard, (sodium carbonate).

TABLE 1

Cholesterol/Lipoprotein Test Results: Adamantyloxy Analogs

| Example No. | Dose Mg/kg | Cholesterol Treated/control ratios | Heparin Precipitating Lipoproteins (HPL) Treated/control ratios |
|---|---|---|---|
| Example 17 | 25 | 0.57 | 0.51 |
| Example 28 | 50 | 0.44 | 0.25 |
| Example 27 | 25 | 0.81 | 0.61 |
| Example 20 | 25 | 0.55 | 0.38 |
| Example 24 | 25 | 0.59 | 0.60 |
| Example 22 | 25 | 0.64 | 0.64 |
| Example 23 | 50 | 0.56 | 0.51 |
| Example 54 | 50 | 0.63 | 0.55 |
| Example 53 | 50 | 0.57 | 0.60 |
| Example 56 | 50 | 0.59 | 0.61 |
| Example 51 | 50 | 0.71 | 0.78 |
| Example 63 | 25 | 0.57 | 0.54 |
| Example 33 | 25 | 0.61 | 0.64 |
| Example 38 | 50 | 0.55 | 0.45 |
| Example 49 | 12.5 | 0.61 | 0.63 |
| Example 13 | 100 | 0.81 | 0.67 |
| Example 10 | 100 | 0.89 | 0.74 |
| Example 72 | 50 | 0.68 | 0.69 |

The compounds (A) of the invention can exist in either the free base form or in the form of an acid addition salt. The acid addition salts are prepared by reacting the free base (A) with a stoichiometric proportion of an appropriate acid such as hydrochloric acid. The method is well known to those skilled in the art and can be carried out in aqueous or non-aqueous media such as ethanol, ether, ethyl acetate and the like.

The pharmaceutically acceptable acid addition salts can be used for the same purposes as the free base. Illustrative of pharmaceutically acceptable acid addition salts are those formed upon reaction of the compounds (A) with hydrochloric acid, hydrobromic acid, sulfuric acid, phosphoric acid, acetic acid, lactic acid, citric acid, succinic acid, benzoic acid, salicyclic acid, pamoic acid, cyclohexanesulfamic acid and the like.

This invention relates also to pharmaceutical dosage unit forms for oral administration which are useful in treating hyperlipidemia or hypercholesteremia in mammals, including humans. The term "dosage unit form" as used in this specification and in the claims refers to physically discrete units suitable as unitary dosages for mammalian subjects, each unit containing a predetermined quantity of the essential active ingredient, i.e.; a compound (A) or a pharmaceutically acceptable acid addition salt thereof, calculated to produce the desired effect in combination with the required pharmaceutical means which adapt said ingredient for oral administration. Examples of dosage unit forms in accordance with this invention are tablets, capsules, orally administered liquid preparations in liquid vehicles, and dry preparations for the extemporaneous preparation in a liquid vehicle. Solid diluents or carriers for the solid oral pharmaceutical dosage unit forms are, for example, selected from the group consisting of lipids, carbohydrates, proteins and mineral solids, for example, starch, sucrose, kaolin, dicalcium phosphate, gelatin, acacia, corn syrup, corn starch, talc and the like. Capsules both hard and soft are formulated with suitable diluents and excipients, for example, edible oils, talc, calcium carbonate and the like and also calcium stearate. Liquid preparations for oral administration are prepared in water or aqueous vehicles which advantageously contain suspending agents, for example, sodium carboxymethylcellulose, methylcellulose, acacia, polyvinyl pyrrolidone, polyvinyl alcohol and the like.

The aforesaid carriers, vehicles, diluents, excipients, preservatives, isotonic agents and the like constitute the pharmaceutical means which adapt the preparations for oral administration.

The effective amount of a compound (A) or the pharmaceutically acceptable acid addition salts thereof required for oral administration to a mammal suffering from hyperlipidemia or hypercholesteremia is that amount which will provide a hypolipidemia or hypocholesteremia effect. The dose can be from about 0.1 to about 10 grams per day, administered singly or in divided doses.

The pharmaceutical dosage unit forms are prepared in accordance with the preceding general description to provide from about 100 mg. to about 5 grams of the essential active ingredient per dosage unit form.

EXAMPLE 106

Suspension

A suspension containing three Gm. of 1-[p-(1-adamantyloxy)phenyl]-pyrrolidine in 15 ml. is prepared from the following:

1-[p-(1-adamantyloxy)phenyl]pyrrolidine: 200 Gm
Sucrose: 400 Gm
Methyl Paraben: 750 mg
Propyl Paraben: 250 mg
Sodium Carboxymethylcellulose: 5 Gm
Polysorbate 80: 500 mg
Distilled water q.s.,: 1,000 ml The suspending agent and surfactant are mixed with some of the water and added to the active ingredient. The parabens and the sucrose are dissolved in hot water and added to the above mixture. The final mixture is diluted to 1000 ml.

One tablespoon is administered orally 3 to 4 times a day in persons with elevated cholesterol levels.

EXAMPLE 107

Tablets

One thousand tablets for oral use, each containing 100 mg. of 1-[p-(1-adamantyloxy)phenyl]pyrroldine, are prepared from the following ingredients:

1-[p-(1-adamantyloxy)phenyl]pyrrolidine: 100 Gm
Methylcellulose U.S.P. (15 cps): 6.5 Gm
Lactose: 25 Gm
Talc: 5 Gm
Calcium Stearate: 3.5 Gm The 1-[p-(1-adamantyloxy)phenyl]pyrrolidine is granulated with 7.5% w/v aqueous solution of methylcellulose, passed through a No. 8 screen and dried carefully. The dried granules are passed through a No. 12 screen, mixed with the talc, lactose and stearate and compressed into tablets.

The foregoing tablets are useful in the treatment of adults with hyperlipidemia at a dose of 4 to 10 tablets daily.

EXAMPLE 108

Capsules

One thousand two-piece hard gelatin capsules for oral use, each capsule containing 250 mg. of 1-[p-(1-adamantyloxy)phenyl]pyrrolidine are prepared from the following ingredients:

1-[p-(1-adamantyloxy)phenyl]pyrrolidine: 250 Gm
Corn Starch: 125 Gm
Talc: 50 Gm
Magnesium Stearate: 5 Gm
Lactose: 20 Gm The finely powdered materials are mixed throughly then filled into hard gelatin capsules of appropriate size.

The foregoing capsules are useful in treatment of adults with elevated cholesterol levels at a dosage of 4 to 8 capsules daily.

EXAMPLE 109

Suspension

One thousand ml. of an oral suspension containing 1 Gm of 1-[p-(1-adamantyloxy)phenyl]pyrrolidine in each 5 ml. is prepared from the following ingredients:

1-[p-(1-adamantyloxy)phenyl]pyrrolidine: 200 Gm
Oil Base, q.s.: 1,000 ml

The oil base consists of equal parts of soybean oil and purified linseed oil gelled with 1% aluminum monostearate. Each 5 ml. of base supplied 1.1 ml. of linolenic acid. One tablespoonful (15 ml.) administered three times a day before meals is useful in treating serum lipid disorders.

EXAMPLE 110

Dispersion

An aqueous oral dispersion, containing in each tablespoonful (15 ml.) 5 gm of 1-[p-(1-adamantyloxy)phenyl]pyrrolidine is prepared from the following ingredients:

1-[p-(1-adamantyloxy)phenyl]pyrrolidine: 5,000 Gm
Pectin, N.F.: 100 gm
Deionized water: 15,000 ml One tablespoon (15 ml.) is given three times a day, with meals, to lower blood cholesterol in hypercholesteremic individuals.

EXAMPLE 111

Powder Packets

Five thousand powder packets each containing 10 Gm of 1-[p-(1-adamantyloxy)phenyl]pyrrolidine are prepared from 50,000 Gm.

One packet emptied into an aqueous vehicle such as water, fruit or vegetable juice, milk, or the like is taken four times a day to reduce the serum sterols in hypercholesteremic patients.

Similar capsules, powder packets, tablets and oil base suspensions useful in reducing hypercholesteremia are prepared as in Examples 106 through 111 utilizing the other compounds (A) disclosed in the examples above.

Preferred compounds are 1-[4-(adamantyloxy)phenyl]pyrrolidine, 1-[4-(adamantyloxy)acetanilide], 1-[4-(adamantyloxy)-2-fluorophenyl]pyrrolidine, and 4'-(1-adamantyloxy)-2'-fluoroacetanilide.

I claim:

1. A compound of the formula

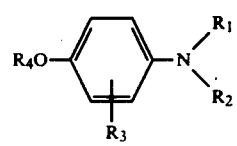

wherein $R_1$ and $R_2$ are the same or different and are hydrogen or alkyl of one to three carbon atoms, inclusive; $R_3$ is hydrogen, fluoro, or chloro; $R_4$ is 1-adamantyl, 2-methyl-2-adamantyl, 1-diamantyl and 4-diamantyl and pharmacologically acceptable acid addition salts thereof.

2. A compound in accordance with claim 1 wherein the compound is a free base.

3. A compound in accordance with claim 1 wherein the compound is a pharmacologically acceptable acid addition salt.

4. A compound in accordance with claim 3 wherein the acid addition salt is hydrochloride.

5. A compound according to claim 1, p-(1-adamantyloxy)aniline.

6. A compound according to claim 1, N-methyl-4-(1-adamantyloxy)aniline hydrochloride.

7. A compound according to claim 1, N-ethyl-4-(1-adamantyloxy)aniline hydrochloride.

8. A compound according to claim 1, N,N-dimethyl-4-(1-adamantyloxy)aniline.

9. A compound according to claim 1, 4-(2-methyl-2-adamantyloxy)aniline.

10. A compound according to claim 1, 4-(1-adamantyloxy)-3-chloroaniline hydrochloride.

11. A compound according to claim 1, 4-(1-adamantyloxy)-2-fluoroaniline.

12. A compound according to claim 1, p-(1-diamantyloxy)aniline.

13. A compound according to claim 1, 4-(1-adamantyloxy)-3-fluoroaniline.

* * * * *